United States Patent
Yi et al.

(10) Patent No.: US 9,593,387 B2
(45) Date of Patent: Mar. 14, 2017

(54) METHOD FOR DETECTING HUMAN PAPILLOMA VIRUS BASED ON SOLEXA SEQUENCING METHOD

(75) Inventors: Xin Yi, Shenzhen (CN); Jiajia Xu, Shenzhen (CN); Xifang Nie, Shenzhen (CN); Meiru Zhao, Shenzhen (CN)

(73) Assignee: BGI GENOMICS CO., LTD, Shenzhen (CN)

( * ) Notice: Subject to any disclaimer, the term of this patent is extended or adjusted under 35 U.S.C. 154(b) by 0 days.

(21) Appl. No.: 13/377,116

(22) PCT Filed: Nov. 15, 2010

(86) PCT No.: PCT/CN2010/001833
§ 371 (c)(1),
(2), (4) Date: Apr. 18, 2012

(87) PCT Pub. No.: WO2012/000151
PCT Pub. Date: Jan. 5, 2012

(65) Prior Publication Data
US 2013/0123114 A1   May 16, 2013

(30) Foreign Application Priority Data
Jun. 30, 2010   (CN) .......................... 2010 1 0213722

(51) Int. Cl.
*C12Q 1/16* (2006.01)
*C12Q 1/70* (2006.01)
*C07H 21/04* (2006.01)
*C12Q 1/68* (2006.01)

(52) U.S. Cl.
CPC .......... *C12Q 1/708* (2013.01); *C12Q 1/6874* (2013.01)

(58) Field of Classification Search
CPC ..................................................... C12Q 1/708
See application file for complete search history.

(56) References Cited

U.S. PATENT DOCUMENTS

| | | | |
|---|---|---|---|
| 2005/0202436 A1 | 9/2005 | Gharizadeh | |
| 2006/0040286 A1* | 2/2006 | Mirkin et al. | 435/6 |
| 2009/0035750 A1* | 2/2009 | Hashimoto et al. | 435/5 |
| 2010/0273219 A1* | 10/2010 | May et al. | 435/91.5 |
| 2011/0276277 A1* | 11/2011 | Lo et al. | 702/20 |

FOREIGN PATENT DOCUMENTS

| | | |
|---|---|---|
| CN | 101435002 A | 5/2009 |
| CN | 101921748 A | 12/2010 |
| CN | 102367490 A | 3/2012 |

OTHER PUBLICATIONS

Carvalho et al., Memorial Institute Oswaldo Cruz, Rio de Janeiro, Feb. 2010, vol. 105(1), pp. 73-78.*
Kozarewa et al., Nature Methods, vol. 6, No. 4, Apr. 2006, pp. 291-295.*
Agarwal, S., Nov. 2005, Manual for Cytology, pp. 1-44.*
Frank, Daniel, BMC Bioinformatics, Oct. 29, 2009, 10:362, pp. 1-13.*

(Continued)

*Primary Examiner* — Samuel Woolwine
(74) *Attorney, Agent, or Firm* — Seed IP Law Group LLP

(57) ABSTRACT

The present invention relates to a method for detecting Human Papilloma Virus (HPV), in particular, to a method for detecting HPV based on Solexa sequencing method.

12 Claims, 1 Drawing Sheet

Illustration of the PCR products labeled by an index and an adapter having a unique characteristic sequence. F: forward PCR primer; R: reverse PCR primers.

(56) References Cited

OTHER PUBLICATIONS

Lo et al., Methods in Molecular Biology, Clinical Applications of PCR, Second Edition, 2006, Humana Press.*
Buck et al., Biotechniques, 1999, 27(3), pp. 528-536.*
Lowe et al. Nucleic Acid Research, 1990, 18(7), pp. 1757-1761.*
Binladen et al., "The Use of Coded PCR Primers Enables High-Throughput Sequencing of Multiple Homolog Amplification Products by 454 Parallel Sequencing," *PloS ONE* 2(e197):1-9, Feb. 2007.
Meyer et al., "Targeted high-throughput sequencing of tagged nucleic acid samples," *Nucleic Acids Research*: 1-5, Aug. 1, 2007.
Brink et al., "HPV detection methods," *Disease Markers*, 23:273-281 (2007).
Cox et al., "HPV DNA testing in cervical cancer screening: From evidence to policies," *Gynecologic Oncology*, 103:8-11 (2006).
Doorbar, "Molecular biology of human papillomavirus infection and cervical cancer," *Clinical Science*, 110:525-541 (2006).
IARC Handbooks of Cancer Prevention, *International Agency for Research on Cancer, World Health Organization*, "Cervix Cancer Screening," IARC Press, (306 pages) (2005).
Kulmala et al., "Human Papillomavirus Testing with the Hybrid Capture 2 Assay and PCR as Screening Tools," *Journal of Clinical Microbiology*, 42(6):2470-2475 (Jun. 2004).
Lozano, "Successfully Integrating Human Papillomavirus Testing Into Your Practice," *Arch Pathol Lab Med*, 127:991-994 (Aug. 2003).
Pectasides et al., "Chemotherapy for recurrent cervical cancer," *Cancer Treatment Reviews*, 34:603-613 (2008).
Quail et al., "A large genome centre's improvements to the Illumina sequencing system," *Nat Methods*, 5(12):1005-1010 (Dec. 2008).
Solexa, Application Note: DNA Sequencing, (2 pages) (2006).
Belinson et al., "A Population-Based Clinical Trial Comparing Endocervical High-Risk HPV Testing Using Hybrid Capture 2 and Cervista From the SHENCCAST II Study," *Am. J. Clin. Pathol.* 135:790-795, 2011.
Belinson et al., "Improved sensitivity of vaginal self-collection and high-risk human papillomavirus testing," *Int. J. Cancer* 130(8):1855-1860, Apr. 15, 2012.
Du et al., "A New PCR-Based Mass Spectrometry System for High-Risk HPV, Part II," *Am. J. Clin. Pathol.* 136:920-923, 2011.
Loman et al., "Performance comparison of benchtop high-throughput sequencing platforms," *Nature Biotechnology* 30:434-439, 2012.
Yu et al., "Application of matrix assisted laser desorption/ionization time-of-flight mass spectrometry on high-risk human papillomavirus detection in clinic," *Chin. J. Lab. Med.* 32(9):1006-1010, Sep. 2009, with English Abstract.

* cited by examiner

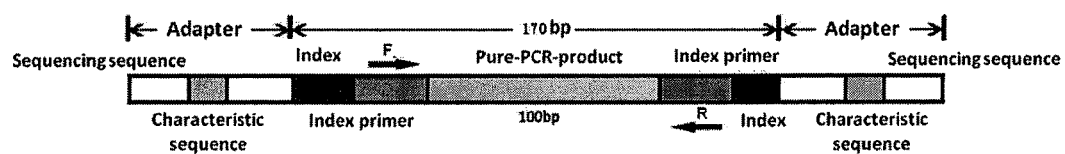
Figure 1: Illustration of the PCR products labeled by an index and an adapter having a unique characteristic sequence. F: forward PCR primer; R: reverse PCR primers.
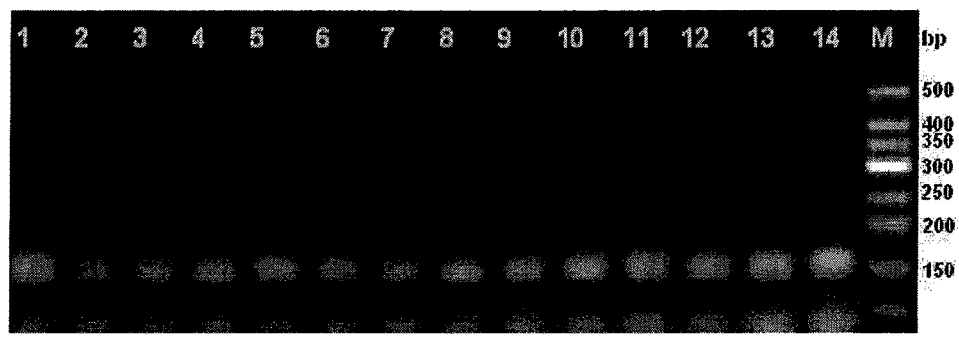
Figure 2: Gel electrophorogram of a part of PCR products.

METHOD FOR DETECTING HUMAN PAPILLOMA VIRUS BASED ON SOLEXA SEQUENCING METHOD

STATEMENT REGARDING SEQUENCE LISTING

The Sequence Listing associated with this application is provided in text format in lieu of a paper copy, and is hereby incorporated by reference into the specification. The name of the text file containing the Sequence Listing is 140175_401USPb_SEQUENCE_LISTING.txt. The text file is 27 KB, was created on Jul. 9, 2012, and is being submitted electronically via EFS-Web.

FIELD OF THE INVENTION

The present invention relates to a method for detecting Human Papilloma Virus (HPV), in particular, to a method for detecting HPV based on Solexa sequencing method.

BACKGROUND OF THE INVENTION

Cervical cancer is the second most common malignant tumor among women in the world, following breast cancer. There are about 500,000 newly reported cases worldwide every year, and nearly 250,000 people die of this disease annually. Cases in developing countries account for approximately ⅔ of the total. Cervical cancer is also prevalent in China. The cases of cervical cancer in China account for 10% of the total. Studies showed that Human Papilloma Virus (HPV) is closely associated with cervical cancer, and is an important carcinogenic factor and one of the prerequisites for causing cervical cancer. It is shown that more than 100 types of HPV can cause infection in skin (skin type) or in mucosa of respiratory tract and anal-genital tract (mucosal type), and more than 40 types of HPV can cause infection in cervices. HPV types are divided into the following two groups depending on the benign, premalignant or malignant pathological changes induced thereby: (1) group of low cancerogenic risk, containing such as types 6, 11, 42, 43, and 44; and (2) group of high cancerogenic risk, containing such as types 16, 18, 31, 33, and 45. Therefore, early detection and correct typing of HPV infections are essential for the prevention and treatment of cervical cancer.

Current HPV detection methods are mainly divided into the following groups. (1) Cytological examination, which makes diagnosis on the basis of change in cell morphology by using cytological examination of cervical smear or thin-prep cell test (TCT). As for HPV infection, koilocytosis, dyskeratosis and condylomata like basal cell can be seen under microscopy. Its shortcoming lies in low sensitivity and specificity in the diagnosis of HPV infection. (2) Immunohistochemical method, which further confirms HPV infection by detecting the capsid antigen of HPV. The positive reaction thus obtained is definitely located and the result is reliable. However, capsid antigens are not produced until HPV-DNA is replicated and mature. Therefore, subjects diagnosed as negative cannot be taken as unaffected by HPV. The method has low sensitivity. (3) Real-time Fluorescence Quantitative PCR (FQ-PCR), which primarily employs a fluorescence detection PCR Instrument. In the method, a fluorescent group is added to the PCR reaction system, and the amplification product produced in each cycle during PCR is real-time monitored by accumulation of the fluorescent signal, thereby accomplishing the quantitation of the initial concentration of the template. The method has a low throughput. (4) Hybrid capture method (primarily HC-II system), which is the only clinic method for detection of HPV DNA approved by US FDA, and is approved by European CE and Chinese SFDA. The method employs specific specimen collectors and containers, a RNA probe of 8000 bp in full length and a specific first antibody, both of which have been granted a patent right. The mechanism for the method is that the nucleic acid probe is hybridized to the HPV DNA of the subject to be tested, and the detection is carried out based on the amplified signals by chemical fluorescence or enzymatic reactions. The nucleic acid probes used in the method are mainly divided into two classes: nucleic acid probes as directed to low-risk HPV and nucleic acid probes as directed to high-risk HPV. The method can be used in primary screening of HPV, but can neither determine the specific type of HPV nor determine multiple infections.

The sensitivity of HPV detection can be increased and the false negative rate can be reduced by using the above detection methods in combination. However, the cost for the combination of these methods was high, and thus the combination of these methods is just feasible in the HPV detection and screening of cervical carcinoma in economy developed areas. For economy less developed areas, especially mountainous areas and most of rural areas, there is a big limitation on using said detection methods in combination. Therefore, there is a need to develop a suitable and low-cost HPV detection method.

In another aspect, the currently known HPV detection methods, such as the detection methods as described above, have low throughput. When conducting HPV detection to samples in large scale, application of said methods are time-consuming and labor-consuming, and the cost thereof is high. Therefore, there is also an urgent need in the art for a new high-throughput and low-cost HPV detection method.

DESCRIPTION OF THE INVENTION

The present invention develops a new HPV detection method and a kit for the same, on the basis of Solexa sequencing method and PCR index. The method and kit according to the present invention can not only achieve a high throughput HPV detection with low cost, but also accomplish accurate HPV typing.

DEFINITION

In order to better understand the present invention, the definitions and explanations of the relevant terms are provided herein.

As used in the application, the term "PCR" refers to polymerase chain reaction.

As used in the application, the term "Solexa sequencing method" refers to a new generation DNA sequencing method, which is developed in current years, also named the second generation sequencing method. The difference between Solexa sequencing method and the traditional sequencing method (such as, Sanger sequencing method) lies in Solexa sequencing method analyses a DNA sequence by conducting sequencing as carrying out synthesis. Solexa sequencing method has the following advantages: 1) low cost, which is 1% of the cost of the traditional sequencing method; 2) high throughput, capable of conducting sequencing to multiple samples simultaneously, and capable of producing a data of about 50 billion (50 G) bases for one Solexa sequencing; 3) high accuracy (greater than 98.4%), which effectively solve the problem relating to readout of poly-repetitive sequences. In another aspect, when the number of the sequences to be sequenced is predetermined, the high sequencing throughput in turn improves the sequencing depth of the sequences (for example, each sequence can be sequenced for more times), thereby ensuring the credibility of the sequencing result. As used in the application, the term "sequencing depth" refers to the times of a fragment of DNA sequence appearing in the sequencing data. Sequencing depth can be calculated by dividing the volume of sequencing data with the length of the genome, for example, a sequencing depth of 10 indicates that the volume of sequencing data is 10 times as the length of the whole genome.

Solexa sequencing method is widely used. It may be applied to genome sequencing, genotype, studies on genetic polymorphism, and the like. In the method according to the present invention, Solexa sequencing method is used to detect HPV: sequencing the samples to be analyzed as directed to HPV, and then aligning the sequencing results with the reference sequences in HPV database by using the alignment programs known in the art, such as BLAST and SOAP, so as to accurately type the HPV infected in the sample. The HPV database used herein comprises the sequences from various HPV types known in the art, which can be found in, for example, public database, such as NCBI database.

As used herein exchangeably, the terms "PCR index", "index", or "primer index" refers to a small fragment of nucleotide sequence being added to the 5' end of a PCR primer, which can be used to label the PCR product by PCR amplification so as to distinguish the template origin of each of the PCR products in the mixture of PCR products of different template origins. PCR products are labeled by adding an index to the 5' end of the primer and using the index primer to carry out amplification, thereby a library for further analysis and treatment can be obtained by mixing multiple different PCR products. Each different PCR product in the library has a unique index, and therefore different PCR products can be distinguished from each other based on the unique index in each PCR product, and the PCR products are corresponded to the PCR templates from which they are amplified one by one.

For example, when multiple samples are to be sequenced, a different index may be added to the 5' end of the primer for each sample, and then PCR reaction is conducted to each sample by using the primer having an index added, thereby labeling each sample (i.e., PCR product). After PCR reaction, a library is constructed by mixing the PCR products carrying different indexes from the samples, and then the PCR products in the library are sequenced by the high-throughput Solexa sequencing method. Finally, in the resultant sequencing data, the sequencing results are corresponded to the PCR products (therefore the sample templates) one by one based on the sequence of the unique indexes.

The index may be introduced into one of the pair of primers for PCR amplification or into both primers of the pair of the primers. When introducing indexes into both primers of the pair of the primers, a pair of PCR primers are combined with a pair of indexes to form a pair of index primers, wherein the forward and reverse PCR primers have a forward and reverse indexes, respectively, and the forward index corresponds to the forward PCR primer and the reverse index corresponds to the reverse PCR primers, and the forward and reverse indexes can be the same or different.

When designing indexes, multiple factors are considered, comprising: 1) single-base repetitive sequences containing 3 or more bases should be avoid in the index sequences; 2) the total content of base A and base C at the same position of all the indexes should be between 30% and 70% of all the bases at the position; for example, when designing 100 different index sequences, the total content of bases A and C at the second position of each of the index sequences (i.e., the so-called same position) should account for 30% to 70% of the bases at the second position of the 100 sequences; 3) GC content of the index sequence per se should be between 40% and 60%; 4) the sequences of the indexes should differ from each other by more than 4 bases; 5) sequences, which are highly similar to the primers for sequencing, should be avoided in the index sequences; 6) after the index sequence is added to the PCR primer, secondary structures such as hairpin structure and dimer should be avoided in PCR index primer.

As used in the application, the term "index primer" refers to a primer carrying an index, which comprises two portions, i.e., the index portion and the primer portion, wherein the index portion is used to label the PCR product in the amplification reaction, while the primer portion base-complementarily matches the template to amplify the template, and the index portion is linked to the 5' end of the primer portion, optionally via a linker sequence.

As used in the application, the term "adapter" or "library adapter" refers to a designed fragment of nucleotide sequence, which may be linked to the amplified PCR product in the library, and therefore all the amplified PCR products in the library can be sequenced by virtue of the adapter, for example, the sequencing is carried out by using the sequencing primer designed as directed to the adapter, without using a specific sequencing primer as directed to the PCR primer. Preferably, the adapter according to the present invention may be linked to the PCR product by "PCR-FREE" methods.

As used in the application, the term "PCR-FREE" refers to a method wherein an adapter is directly linked to a PCR product without performing PCR reaction, for example, an adapter is linked to a PCR product by using a DNA ligase. It is known for a person skilled in the art to construct a sequencing library by using PCR-Free methods (See, for example, Nature Methods 6, 291-295 (2009)). "PCR-FREE" methods have the following advantages as PCR are not necessary during the whole process: 1) reducing purification steps, reducing the time and cost spent; 2) reducing non-specific amplification; 3) avoiding mistakes introduced by PCR during construction of a library comprising a lot of PCR products of which the sequences are highly homologous, thereby improving the accuracy of the final sequencing results.

As used in the application, the method and kit according to the present invention may employ at least 1 adapter. Different adapters may share a fragment of the same sequence (cited herein as "sequencing sequence"), and can further comprise a different characteristic sequence, and therefore different adapters can be sequenced by the same primer (which is designed as directed to the same sequencing sequence), and the unique characteristic sequence can be used to distinguish the library origin of each of the PCR products in the mixture of multiple libraries, i.e., further labeling the PCR products of different library origins.

The labeling efficiency is greatly improved by the combination of indexes with adapters having different characteristic sequences (see FIG. 1). For example, 100 indexes can label 100 samples, while the combinations of 100 indexes and 200 adapters with different characteristic sequences can label 100*200=20000 samples.

Therefore, in one aspect, the present invention provides a group of indexes, comprising at least 10, preferably at least 20, at least 30, at least 40, at least 50, at least 60, at least 70, at least 80, at least 90 or 95 indexes, and said indexes have the sequences selected from the group consisting of SEQ ID NOS: 1-95. In a preferred embodiment, the group of indexes comprises at least the indexes set forth in SEQ ID NOS: 1-10, or SEQ ID NOS: 11-20, or SEQ ID NOS: 21-30, or SEQ ID NOS: 31-40, or SEQ ID NOS: 41-50, or SEQ ID NOS: 51-60, or SEQ ID NOS: 61-70, or SEQ ID NOS: 71-80, or SEQ ID NOS: 81-90, or SEQ ID NOS: 91-95, or any combination thereof, for example, the indexes set forth in SEQ ID NOS: 1-95.

In a preferred embodiment according to the present invention, the indexes according to the present invention are used to label the PCR primers set forth in SEQ ID NOS: 96-106, and therefore are used to carry out high-throughput HPV sequencing, detection or typing.

In one aspect, the present invention provides an index primer group, comprising 11 index primers, the sequence of said index primer comprises an is index sequence and a PCR primer sequence, and the index sequence is linked to 5' end of the PCR primer sequence, optionally via a linker sequence, wherein
1) said index sequence is selected from the group consisting of SEQ ID NOS: 1-95, and each of said 11 index primers in the index primer group has the same index sequence, and
2) the PCR primer sequences of said 11 index primers are set forth in SEQ ID NOS: 96-106, respectively.

The index primer group according to the present invention can amplify at least 16 products of about 170 bp, which correspond to a highly conserved DNA sequence in the most conserved gene region (L1 region) of HPV genome. Therefore, the index primer group according to the present invention can be used to accurately type HPV.

In a preferred embodiment, the index primer group according to the present invention is useful in HPV sequencing, detection or typing, and therefore is useful in medical use, such as diagnosis of the presence of HPV and determination of HPV types, and non-medical use, such as construction of HPV database, identification of a new HPV type and subtype, study on regional characteristics of distribution of HPV types, study on epidemiology and development of vaccines. In another preferred embodiment, the index primer group according to the present invention can be used in manufacture of a kit useful in HPV sequencing, detection or typing.

In another aspect, the present invention provides an index primer set, comprising at least 10, preferably at least 20, at least 30, at least 40, at least 50, at least 60, at least 70, at least 80, at least 90 or 95 index primer groups as described above. Preferably, in the index primer set, the index sequences used in the different index primer groups are different. More preferably, the index sequences used in the index primer set comprise at least the index sequences set forth in SEQ ID NOS: 1-10, or SEQ ID NOS: 11-20, or SEQ ID NOS: 21-30, or SEQ ID NOS: 31-40, or SEQ ID NOS: 41-50, or SEQ ID NOS: 51-60, or SEQ ID NOS: 61-70, or SEQ ID NOS: 71-80, or SEQ ID NOS: 81-90, or SEQ ID NOS: 91-95, or any combination thereof, such as the index sequences set forth in SEQ ID NOS: 1-95.

In a preferred embodiment, the index primer set according to the present invention is useful in high-throughput HPV sequencing, detection or typing, and therefore useful in medical use, such as diagnosis of HPV associated diseases and accurate determination of HPV types (which provides basis for clinic diagnosis and treatment scheme) on large-scale, and non-medical use, such as construction of HPV database, identification of a new HPV type and subtype, study on regional characteristics of distribution of HPV types, study on epidemiology and development of vaccines. In another preferred embodiment, the index primer set according to the present invention can be used in manufacture of a kit useful in HPV sequencing, detection or typing.

In another aspect, the present invention provides a kit comprising the index primer group or index primer set as described above. Preferably, the kit according to the present invention further comprises at least 1, preferably at least 2, at least 10, at least 20, at least 30, at least 40, at least 50, at least 100 or at least 200 adapters. In a preferred embodiment, the adapter is suitable for Solexa sequencing method; for example, the adapter is useful in construction of a sequencing library, for example, said adapters can have the sequences selected from the group consisting of SEQ ID NOS: 121-132. In a preferred embodiment, adapters are used to construct a sequencing library by PCR-FREE methods, such as DNA ligase assay.

In a preferred embodiment, the kit according to the present invention is useful in high-throughput HPV sequencing, detection or typing, and useful in medical use and non-medical use as described above.

In another aspect, the present invention provides a method for sequencing, detecting, or typing HPV in one or more samples. The method comprises the steps of amplifying DNA in each sample using an index primer group or an index primer set or a kit as described above, and then sequencing to obtain the sequence of the sample.

In another aspect, the present invention provides a method for sequencing, detecting, or typing HPV in one or more samples, comprising the following steps:
providing n samples, wherein n is an integer of ≥1, said samples preferably are from mammals, more preferably from human, and preferably are exfoliative cells; optionally, the n samples to be analyzed are divided into m groups, wherein m is an integer and n≥m≥1;
1) for each sample, amplifying DNA in the sample with one index primer group, wherein said index primer group comprises 11 index primers, the sequence of said index primer comprises an index sequence and a PCR primer sequence, and the index sequence is linked to 5' end of the PCR primer sequence, optionally via a linker sequence, wherein
  i) said index sequence is selected from the group consisting of SEQ ID NOS: 1-95, and each of said 11 index primers has the same index sequence, and
  ii) the PCR primer sequences of said 11 index primers are set forth in SEQ ID NOS: 96-106, respectively,
wherein the index primer groups used in different samples can be the same or different, and different index primer groups employ different index sequences;
2) mixing the amplification products obtained by conducting amplification with different index primer groups in step 1), so as to obtain one or more PCR product libraries;
3) adding an adapter to one or more PCR product libraries obtained in step 2) by PCR-FREE methods such as DNA ligase assay, thereby constructing one or more sequencing libraries, wherein the adapters used in different sequencing libraries may be the same or different, and different adapters share the same sequencing sequence but have different characteristic sequences,
4) optionally, mixing the sequencing libraries with different adapters as obtained in step 3), so as to obtain one or more library mixtures;

5) conducting sequencing to one or more sequencing libraries obtained in step 3) or one or more library mixtures obtained in step 4) by using the second generation sequencing technology, preferably Pair-End technology (such as Solexa, Illumina Hiseq 2000);

6) corresponding the sequencing results to the samples one by one, according to the index primer sequences of the index primer group or according to the index primer sequences of the index primer group and the characteristic sequence of the adapter;

wherein said samples are preferably exfoliative cells and are preferably from animals, such as human.

In preferred embodiments, at least 10, preferably at least 20, at least 30, at least 40, at least 50, at least 60, at least 70, at least 80, at least 90 or 95 index primer groups as described above are used in the method according to the present invention. Further preferably, the index sequences used comprise at least the index sequences set forth in SEQ ID NOS: 1-10, or SEQ ID NOS: 11-20, or SEQ ID NOS: 21-30, or SEQ ID NOS: 31-40, or SEQ ID NOS: 41-50, or SEQ ID NOS: 51-60, or SEQ ID NOS: 61-70, or SEQ ID NOS: 71-80, or SEQ ID NOS: 81-90, or SEQ ID NOS: 91-95, or any combination thereof, for example, the index sequences set forth in SEQ ID NOS: 1-95.

In a preferred embodiment, at least 1, preferably at least 2, at least 10, at least 20, at least 30, at least 40, at least 50, at least 100 or at least 200 adapters are used in the method according to the present invention, and for example, said adapter may have the sequence selected from the group consisting of SEQ ID NOS: 121-132.

In a preferred embodiment of the method according to the present invention, after sequencing, the sequences obtained from the sample is aligned with the sequence in HPV database, so as to accurately type HPV in the sample.

In another aspect of the present invention, the present invention provides a method for high-throughput HPV sequencing, detecting or typing in multiple samples based on Solexa sequencing method, comprising the following steps:

1) dividing the samples to be analyzed into m groups, m is an integer of ≥1;

2) carrying out the following steps to the samples in each group:
  2a) extracting DNA from the sample to be analyzed;
  2b) designing a set of indexes on the basis of the sequences of all the primers in the primer group for amplifying HPV DNA, wherein the number of the indexes, i.e., n, is equal to the number of the samples in the group;
  2c) adding each of the indexes designed in step 2b) to the 5' end of the sequences of all the forward primers or reverse primers or all the primers, respectively, thereby providing n index primer groups;
  2d) conducting PCR amplification to the DNA sample obtained in step 2a) by using the index primer group provided in step 2c), thereby providing PCR products, wherein a different index primer group is used for each DNA sample; and
  2e) mixing all the PCR products in step 2d), so as to obtain a PCR product library;

3) adding an adapter to the PCR product library obtained in step 2), wherein each of the PCR product libraries uses a different adapter so as to m construct m sequencing libraries, wherein each adapter shares the same sequencing sequence and has a different characteristic sequence;

4) mixing m sequencing libraries, conducting sequencing by using the second generation sequencing technology, preferably Pair-End technology, such as Solexa and Illumina Hiseq 2000 sequencing, so as to obtain the sequencing results of all the samples;

5) corresponding the sequencing results to the samples one by one, according to the characteristic sequences of the adapters, the sequences of the indexes, and the sequences of the primers in the sequencing results; and optionally, aligning the sequencing result of each sample with the HPV database, so as to achieve HPV sequencing, detection or typing;

wherein said samples are preferably exfoliative cells and are preferably from animals, such as human.

In a preferred embodiment, DNA is extracted by a method well known to a person skilled in the art. For example, DNA extraction can be carried out by using automatic DNA extractor and DNA extracting kit, for example, commercially available KingFisher automatic extractor, and US Thermo Scientific Kingfisher Flex full automatic bead extraction and purification system.

In a preferred embodiment, the primer group in step 2b) comprises 11 primers, of which the sequences are set forth in SEQ ID NOS: 96-106, respectively. The primer group consisting of 11 primers can be used to amplify to obtain at least 16 products of about 170 bp, which correspond to a highly conserved DNA sequence in the most conserved gene region (L1 region) of HPV genome. Therefore, accurate HPV typing can be accomplished by accurately sequencing the amplification product.

In another preferred embodiment, the number of the indexes designed in step 2b) is at least 10, preferably at least 20, at least 30, at least 40, at least 50, at least 60, at least 70, at least 80, at least 90, or at least 100. Preferably, the index has the sequence selected from the group consisting of SEQ ID NOS: 1-95. In preferred embodiments, the indexes used in different groups of samples may be the same or different. In preferred embodiments, the index introduced into the forward primer may be the same as or different from the index introduced into the reverse primer. In specially preferred embodiments, is the indexes designed in step 2b) comprises at least the indexes set forth in SEQ ID NOS: 1-10, or SEQ ID NOS: 11-20, or SEQ ID NOS: 21-30, or SEQ ID NOS: 31-40, or SEQ ID NOS: 41-50, or SEQ ID NOS: 51-60, or SEQ ID NOS: 61-70, or SEQ ID NOS: 71-80, or SEQ ID NOS: 81-90, or SEQ ID NOS: 91-95, or any combination thereof. In specially preferred embodiments, the indexes designed in step 2b) are set forth in SEQ ID NOS: 1-95.

In a preferred embodiment, adapters are added to PCR product libraries by PCR-FREE methods, for example, using DNA ligase. In particular, in the method according to the present invention, since the DNA sequences of different HPV types are highly homologous, the construction of the sequencing library according to the present invention has to be accomplished by PCR-FREE methods. On the contrary, if adapters are added to PCR products to construct a sequencing library by the conventional pooling PCR, the resultant library will comprise a lot of products inconsistent with the original templates, resulting in being unable to accurately sequence the original templates. In a preferred embodiment, the number of the adapters used is at least 1, at least 2, at least 10, at least 20, at least 30, at least 40, at least 50, at least 100 or at least 200, and for example, said adapter may have the sequence selected from the group consisting of SEQ ID NOS: 121-132.

In preferred embodiments of the method according to the present invention, the adapters are commercially available adapters, such as PCR-free Index Adapter Oligo Mix purchased from Illumina Company. In another embodiments, the present invention can also use the following PCR-free adapters (the portion underlined is the characteristic sequence of the adapter).

```
PCR-free adapter 1 (SEQ ID NO: 121):
5-Phos/GATCGGAAGAGCACACGTCTGAACTCCAGTCACATCACGAT

CTCGTATGCCGTCTTCTGCTTG

PCR-free adapter 2 (SEQ ID NO: 122):
5-Phos/GATCGGAAGAGCACACGTCTGAACTCCAGTCACCGATGTAT

CTCGTATGCCGTCTTCTGCTTG

PCR-free adapter 3 (SEQ ID NO: 123):
5-Phos/GATCGGAAGAGCACACGTCTGAACTCCAGTCACTTAGGCAT

CTCGTATGCCGTCTTCTGCTTG

PCR-free adapter 4 (SEQ ID NO: 124):
5-Phos/GATCGGAAGAGCACACGTCTGAACTCCAGTCACTGACCAAT

CTCGTATGCCGTCTTCTGCTTG

PCR-free adapter 5 (SEQ ID NO: 125):
5-Phos/GATCGGAAGAGCACACGTCTGAACTCCAGTCACACAGTGAT

CTCGTATGCCGTCTTCTGCTTG

PCR-free adapter 6 (SEQ ID NO: 126):
5-Phos/GATCGGAAGAGCACACGTCTGAACTCCAGTCACGCCAATAT

CTCGTATGCCGTCTTCTGCTTG

PCR-free adapter 7 (SEQ ID NO: 127):
5-Phos/GATCGGAAGAGCACACGTCTGAACTCCAGTCACCAGATCAT

CTCGTATGCCGTCTTCTGCTTG

PCR-free adapter 8 (SEQ ID NO: 128):
5-Phos/GATCGGAAGAGCACACGTCTGAACTCCAGTCACACTTGAAT

CTCGTATGCCGTCTTCTGCTTG

PCR-free adapter 9 (SEQ ID NO: 129):
5-Phos/GATCGGAAGAGCACACGTCTGAACTCCAGTCACGATCAGAT

CTCGTATGCCGTCTTCTGCTTG

PCR-free adapter 10 (SEQ ID NO: 130):
5-Phos/GATCGGAAGAGCACACGTCTGAACTCCAGTCACTAGCTTAT

CTCGTATGCCGTCTTCTGCTTG

PCR-free adapter 11 (SEQ ID NO: 131):
5-Phos/GATCGGAAGAGCACACGTCTGAACTCCAGTCACGGCTACAT

CTCGTATGCCGTCTTCTGCTTG

PCR-free adapter 12 (SEQ ID NO: 132):
5-Phos/GATCGGAAGAGCACACGTCTGAACTCCAGTCACCTTGTAAT

CTCGTATGCCGTCTTCTGCTTG
```

In a preferred embodiment, Solexa sequencer (such as Illumina Genome Analyzer II x sequencer) is used in the method according to the present invention to carry out Solexa sequencing. In another preferred embodiment, HPV database comprises the sequences of HPV types known in the art, which for example, can be found in public databases such as NCBI database.

In a preferred embodiment of the method according to the present invention, the samples may be exfoliative cells. In another preferred embodiment, the samples may be from animals, preferably mammals, more preferably human.

BENEFICIAL EFFECT OF THE PRESENT INVENTION

The new method for detecting HPV according to the present invention and the kit for the same have the following advantages over the prior art.

1) High throughput. The detection of even 10000 samples can be accomplished by carrying out the method according to the present invention once using indexes and adapters with different characteristic sequences. Therefore, the method according to the present invention can be widely applied to disease survey and become an efficient means for early diagnosis of diseases.

2) Low cost. The present invention conducts sequencing by Solexa sequencing method, the cost for sequencing is greatly reduced (only accounting for 1% of the cost of the conventional sequencing methods), thereby greatly reducing the cost for HPV detection.

3) Accurate typing of HPV. The types of HPV can be accurately determined by carrying out amplification using multiple primers (such as 6 forward primers and 5 reverse primers according to the present invention) and aligning the sequence information of the amplification products with the HPV database, thereby providing basis for clinic diagnosis and selection of treatment scheme.

In addition, the method according to the present invention also facilitate the discovery of new HPV types, including new subtypes and variants of known types, and provides a more efficient and convenient tool for scientific studies.

The preferable embodiments according to the present invention are described in detail below by combining the drawings with the Examples. However, a person skilled in the art will understand that the following drawings and Examples are intended to illustrate the present invention only, instead of limiting the scope of the present invention. According to the drawings and the detailed description of the preferred embodiments, the purposes and advantages of the present invention are obvious for a person skilled in the art.

DESCRIPTION OF THE DRAWINGS

FIG. 1 is an illustration of the PCR products labeled by an index and an adapter having a unique characteristic sequence. In an exemplary method according to the present invention, indexes are added simultaneously to both ends of the PCR products from each sample by PCR, and multiple PCR products carrying different indexes are mixed together to construct a sequencing library. During the construction of the sequencing library, if necessary, multiple sequencing libraries can be constructed, wherein adapters carrying different characteristic sequences are used to label the sequencing libraries. After construction of libraries is finished, multiple libraries labeled is by adapters carrying different characteristic sequences are mixed together and are sequenced simultaneously by Solexa sequencing method (the indexes used in different sequencing libraries may be the same or different). Finally, according to the sequence information of the characteristic sequences of the adapters and indexes in the sequencing results, the sequencing results can be corresponded to the samples one by one.

FIG. 2 is an agarose gel electrophorogram of a part of PCR products. It can be seen from the electrophorogram that the band of the PCR products is of about 170 bp, wherein lane M is a molecular ladder of 50 bp DNA, lanes 1-14 refer to the PCR products from the randomly selected HPV positive samples.

EXAMPLES 190 samples, of which the HC-II results are known, were genotyped for HPV by the method according to the present invention. The results showed that the results obtained by the method according to the present invention are not only consistent with the known HC-II results, but also accomplish the accurate typing of HPV.

Example 1

Exaction of DNA Samples

According to the instruction of the manufacturer, KingFisher automatic extractor (US Thermo Scientific Kingfisher Flex full automatic bead extraction and purification system) was used to extract DNA from 190 samples of exfoliative cells, of which the HC-II results are known. The nucleic acids were extracted by using the program "Bioeasy_200 μl Blood DNA_KF.msz". After the program was finished, about 100 μl eluting product (extracted DNA) was obtained, which was used as the template for PCR amplification in next step.

Example 2

PCR Amplification

The 190 DNA samples obtained in Example 1 were designated as No. 1-190, and were divided averagely into two groups (HPV-1 group: Nos. 1-95; HPV-2 group: Nos. 96-190). According to the sequences (Table 2, SEQ ID NOS: 96-106) of the primers in the primer group for amplification of HPV DNA (including 6 forward primers and 5 reverse primers), a set of indexes was designed, including 95 indexes (Table 1, SEQ ID NOS: 1-95). Each of the designed indexes was added to the 5' end of the sequence of each primer of the primer set, respectively, thereby obtaining 95 index primer groups, wherein each index primer group included the corresponding 6 forward index primers and 5 reverse index primers, and different index primer groups employed different indexes (i.e., 95 index primer groups were corresponded to 95 indexes one by one).

PCR reactions were conducted for all the samples in the 96-well plates, and two plates were used (one for HPV-1 group and the other for HPV-2 group). DNA obtained in Example 1 was used as template, and a different index primer group was used to carry out PCR amplification as directed to each of the samples in HPV-1 group and HPV-2 group (each containing 95 samples), that is, 95 samples were corresponded to 95 index primer groups one by one. The number of the sample corresponding to each index primer group (each index) was recorded. In each plate, a negative control was provided without adding template. The primers used in the negative controls in the two plates were the same as the primers used in sample No. 1 and No. 96, respectively.

TABLE 1

Information on indexes and samples

| Index No. | Index sequences | The corresponding position in the 96-well plate | The corresponding sample (Group 1) | The corresponding sample (Group 2) | SEQ ID NO: |
|---|---|---|---|---|---|
| PI-1 | GCTGCGACTC | A1 | 1 | 96 | 1 |
| PI-2 | GTGTAGATAC | A2 | 2 | 97 | 2 |
| PI-3 | CTGATATCTA | A3 | 3 | 98 | 3 |
| PI-4 | ACGATGCTAT | A4 | 4 | 99 | 4 |
| PI-5 | TAGACTAGAC | A5 | 5 | 100 | 5 |
| PI-6 | CTGTCTGTGT | A6 | 6 | 101 | 6 |
| PI-7 | GCATACTGAC | A7 | 7 | 102 | 7 |
| PI-8 | CTGCTCGCAT | A8 | 8 | 103 | 8 |
| PI-9 | CATGAGTAGA | A9 | 9 | 104 | 9 |
| PI-10 | TCTCACTATG | A10 | 10 | 105 | 10 |
| PI-11 | TGTACTACTA | A11 | 11 | 106 | 11 |
| PI-12 | GTAGACTAGT | A12 | 12 | 107 | 12 |
| PI-13 | ATATGCTACT | B1 | 13 | 108 | 13 |
| PI-14 | CACTCGCTGT | B2 | 14 | 109 | 14 |
| PI-15 | CATCACGCAC | B3 | 15 | 110 | 15 |
| PI-16 | AGCATGTGAT | B4 | 16 | 111 | 16 |
| PI-17 | AGCTAGTAGA | B5 | 17 | 112 | 17 |
| PI-18 | GCTATGTAGT | B6 | 18 | 113 | 18 |
| PI-19 | TACGATGATG | B7 | 19 | 114 | 19 |
| PI-20 | TACGCTGTAC | B8 | 20 | 115 | 20 |
| PI-21 | TATGTGTACT | B9 | 21 | 116 | 21 |

TABLE 1-continued

Information on indexes and samples

| Index No. | Index sequences | The corresponding position in the 96-well plate | The corresponding sample (Group 1) | The corresponding sample (Group 2) | SEQ ID NO: |
|---|---|---|---|---|---|
| PI-22 | TGACTCAGAC | B10 | 22 | 117 | 22 |
| PI-23 | TCGTAGCTCA | B11 | 23 | 118 | 23 |
| PI-24 | GAGACTCGTA | B12 | 24 | 119 | 24 |
| PI-25 | CTAGATGTCA | C1 | 25 | 120 | 25 |
| PI-26 | GATGACTCTC | C2 | 26 | 121 | 26 |
| PI-27 | TCAGTCGCAC | C3 | 27 | 122 | 27 |
| PI-28 | TGTAGTGAGT | C4 | 28 | 123 | 28 |
| PI-29 | TCATCGTAGA | C5 | 29 | 124 | 29 |
| PI-30 | TAGCATCTGT | C6 | 30 | 125 | 30 |
| PI-31 | TAGTAGTCGT | C7 | 31 | 126 | 31 |
| PI-32 | CTATACGTGC | C8 | 32 | 127 | 32 |
| PI-33 | CGACTGTAGA | C9 | 33 | 128 | 33 |
| PI-34 | ATGTCATGT | C10 | 34 | 129 | 34 |
| PI-35 | GTCTCGACTG | C11 | 35 | 130 | 35 |
| PI-36 | AGCTGACGAT | C12 | 36 | 131 | 36 |
| PI-37 | ATGATATAGT | D1 | 37 | 132 | 37 |
| PI-38 | ATGTGCTCTA | D2 | 38 | 133 | 38 |
| PI-39 | CTCACTCGAT | D3 | 39 | 134 | 39 |
| PI-40 | GCTGCGACTC | D4 | 40 | 135 | 40 |
| PI-41 | GAGTCATGTC | D5 | 41 | 136 | 41 |
| PI-42 | CATACGCTCA | D6 | 42 | 137 | 42 |
| PI-43 | CACTCTCGTC | D7 | 43 | 138 | 43 |
| PI-44 | GCACTAGATG | D8 | 44 | 139 | 44 |
| PI-45 | AGTACGCATG | D9 | 45 | 140 | 45 |
| PI-46 | TCTGTGACGT | D10 | 46 | 141 | 46 |
| PI-47 | TAGCTCATCT | D11 | 47 | 142 | 47 |
| PI-48 | AGCATACACT | D12 | 48 | 143 | 48 |
| PI-49 | GCTATAGTCA | E1 | 49 | 144 | 49 |
| PI-50 | CGTCTCATGC | E2 | 50 | 145 | 50 |
| PI-51 | GCTACTACGT | E3 | 51 | 146 | 51 |
| PI-52 | GAGTGTACTA | E4 | 52 | 147 | 52 |
| PI-53 | GTCATACGTG | E5 | 53 | 148 | 53 |
| PI-54 | TATGAGAGAT | E6 | 54 | 149 | 54 |
| PI-55 | ATCTGAGTAC | E7 | 55 | 150 | 55 |
| PI-56 | CGATAGCATC | E8 | 56 | 151 | 56 |

TABLE 1 -continued

Information on indexes and samples

| Index No. | Index sequences | The corresponding position in the 96-well plate | The corresponding sample (Group 1) | The corresponding sample (Group 2) | SEQ ID NO: |
|---|---|---|---|---|---|
| PI-57 | ACTGATCTCA | E9 | 57 | 152 | 57 |
| PI-58 | CTCGATACTA | E10 | 58 | 153 | 58 |
| PI-59 | CATGTGACTG | E11 | 59 | 154 | 59 |
| PI-60 | CGCATCACTA | E12 | 60 | 155 | 60 |
| PI-61 | GCATATATCT | F1 | 61 | 156 | 61 |
| PI-62 | CTGATGCGAC | F2 | 62 | 157 | 62 |
| PI-63 | TCTCAGAGTC | F3 | 63 | 158 | 63 |
| PI-64 | CAGTGCGAGT | F4 | 64 | 159 | 64 |
| PI-65 | ATCTCTGATG | F5 | 65 | 160 | 65 |
| PI-66 | GCTAGTAGTC | F6 | 66 | 161 | 66 |
| PI-67 | ATGAGTCGTC | F7 | 67 | 162 | 67 |
| PI-68 | ATCACTCAGA | F8 | 68 | 163 | 68 |
| PI-69 | TCTCTCTGAT | F9 | 69 | 164 | 69 |
| PI-70 | CTCTAGTGCT | F10 | 70 | 165 | 70 |
| PI-71 | CGTCGTGCTA | F11 | 71 | 166 | 71 |
| PI-72 | CGACTACTAT | F12 | 72 | 167 | 72 |
| PI-73 | GCACGTCGAT | G1 | 73 | 168 | 73 |
| PI-74 | GTAGTGCTCT | G2 | 74 | 169 | 74 |
| PI-75 | CTGACGAGCT | G3 | 75 | 170 | 75 |
| PI-76 | CTATAGTCTA | G4 | 76 | 171 | 76 |
| PI-77 | ACACGCACTA | G5 | 77 | 172 | 77 |
| PI-78 | CTCGCACTAC | G6 | 78 | 173 | 78 |
| PI-79 | AGATCTCACT | G7 | 79 | 174 | 79 |
| PI-80 | ATACTAGTGT | G8 | 80 | 175 | 80 |
| PI-81 | ATATCTCGTA | G9 | 81 | 176 | 81 |
| PI-82 | TGACTGCGTA | G10 | 82 | 177 | 82 |
| PI-83 | TGTAGACGTA | G11 | 83 | 178 | 83 |
| PI-84 | AGAGACTATG | G12 | 84 | 179 | 84 |
| PI-85 | GTCGAGTCAC | H1 | 85 | 180 | 85 |
| PI-86 | TGACAGCTAC | H2 | 86 | 181 | 86 |
| PI-87 | CGCTAGACAT | H3 | 87 | 182 | 87 |
| PI-88 | CGTAGATATG | H4 | 88 | 183 | 88 |
| PI-89 | TGAGTCTGCT | H5 | 89 | 184 | 89 |
| PI-90 | TAGTCGTATG | H6 | 90 | 185 | 90 |
| PI-91 | CATACACGAC | H7 | 91 | 186 | 91 |
| PI-92 | CGCTCAGAGA | H8 | 92 | 187 | 92 |

TABLE 1 -continued

Information on indexes and samples

| Index No. | Index sequences | The corresponding position in the 96-well plate | The corresponding sample (Group 1) | The corresponding sample (Group 2) | SEQ ID NO: |
|---|---|---|---|---|---|
| PI-93 | GTGAGTCTCA | H9 | 93 | 188 | 93 |
| PI-94 | GACAGATGAT | H10 | 94 | 189 | 94 |
| PI-95 | GCTGTGCGAC | H11 | 95 | 190 | 95 |

TABLE 2

The sequence information of the primers of the primer group for amplification of HPV DNA without adding indexes.

| Primer No. | Primer sequence | SEQ ID NO: |
|---|---|---|
| F1 | TTTGTTACTGTGGTAGATACTAC | 96 |
| F2 | TTTGTTACTGTGGTGGATACTAC | 97 |
| F3 | TTTGTTACCGTTGTTGATACTAC | 98 |
| F4 | TTTGTTACTAAGGTAGATACCACTC | 99 |
| F5 | TTTGTTACTGTTGTGGATACAAC | 100 |
| F6 | TTTGTTACTATGGTAGATACCACAC | 101 |
| R1 | GAAAAATAAACTGTAAATCATATTCCT | 102 |
| R2 | GAAAAATAAATTGTAAATCATACTC | 103 |
| R3 | GAAATATAAATTGTAAATCAAATTC | 104 |
| R4 | GAAAAATAAACTGTAAATCATATTC | 105 |
| R5 | GAAAAATAAACTGCAAATCATATTC | 106 |

Note:
F represents a forward primer,
R represents a reverse primer.

The following PCR parameters were used in amplification:

95° C. 30 s→48° C. 30 s→72° C. 30 s (40 cycles)
72° C. 10 min→12° C. ∞

PCR reaction system was of 25 µl, and its composition was as follows (all the agents were purchased from Enzymatics Company):

| agents | volume/reaction |
|---|---|
| H₂O (HPLC grade) | 14.375 µl |
| 10x Ex Taq Buffer (Mg²⁺ plus) | 2.5 µl |
| dNTP mix (each 2.5 mM) | 2 µl |
| mixture of F1/F2/F3/F4/F5/F6 carrying an index (each 7.5 pmol) | 0.5 µl |
| mixture of R1/R2/R3/R4/R5 carrying an index (each 7.5 pmol) | 0.5 µl |
| Ex Taq HS (5 U/µl) | 0.125 µl |
| Template DNA | 5 µl |
| Total volume | 25 µl |

PCR reaction was carried out in PTC-200 PCR Instrument from Bio-Rad Company. After finishing PCR, 3 µl PCR product was taken to perform electrophoresis on 2.5% agarose gel (FIG. 2).

Example 3

Mixing and Purification of PCR Products

The rest PCR products in HPV-1 group and HPV-2 group each were mixed in a 3 ml EP tube (also marked as HPV-1 group and HPV-2 group), and were mixed homogenously under shaking. 500 µl DNA was taken from each of the two tubes, and was purified by using the Qiagen DNA Purification kit according to the instruction of the manufacturer, to provide 200 µl purified DNA. The DNA concentrations of the purified mixtures were determined as 98 ng/µl (HPV-1 group) and 102 ng/µl (HPV-2 group) by using Nanodrop 8000 (Thermo Fisher Scientific Co.), respectively.

Example 4

Construction of Solexa Sequencing Library 4.1: End-Repair Reaction

DNA end-repair reaction was conducted to the purified DNA mixtures in the two tubes obtained in Example 3 by using Thermomixer (Eppendorf Company), respectively. The reaction system for the repair reaction was of 100µl and its composition was as follow (all the agents were purchased from Enzymatics Company):

| Agents | Volume/reaction |
|---|---|
| DNA obtained in last step | 75 µl |
| 20x Polynucleotide Kinase Buffer(B904) | 10 µL |
| dNTP mix (20 mM each) | 4 µL |
| T4 DNA Polymerase | 5 µL |
| Klenow Fragment | 1 µL |
| T4 Polynucleotide Kinase | 5 µL |
| Total volume | 100 µL |

Reaction condition: 20° C., 30 mins.

According to the instruction of the manufacturer, the products of the DNA end-repair reaction were purified and recovered by using QIAquick PCR Purification kit. The recovered product was dissolved in 34 µl EB (QIAGEN Elution Buffer).

4.2: Addition of A at the 3' End

The base A was added to the 3' end of the recovered DNA by using Thermomixer (Eppendorf Company). The reaction system was of 50 ul, and its composition was as follow (all the agents were purchased from Enzymatics Company):

| Agent | Volume/reaction |
| --- | --- |
| DNA obtained in last step | 32 μl |
| dATP (1 mM, GE Company) | 10 μl |
| 10x Blue Buffer | 5 μl |
| Klenow (3'-5'exo–) | 3 μl |
| Total volume | 50 μl |

Reaction conditions: 37° C., 30 mins.

According to the instruction of the manufacturer, the product having the base A added at 3' end was purified and recovered by using MiniElute PCR Purification Kit (QIAGEN Company). The recovered product was dissolved in 20 μl EB.

4.3: Addition of Solexa Adapter

Different adapters were added to the two products obtained in last step by using Thermomixer (Eppendorf Company), so as to construct 2 sequencing libraries. The corresponding correlation between the adapters and libraries was recorded.

The reaction system for the addition of the Solexa adapters was of 50 ul, and its composition was as follow (all the agents were purchased from Illumina Company):

| Agent | Volume/reaction |
| --- | --- |
| DNA obtained in last step | 11 μL |
| 2x Rapid ligation Buffer | 15 μL |
| PCR-free Index Adapter oligo mix (25 mM) | 1 μL |
| T4 DNA Ligase (Rapid, L603-HC-L) | 3 μL |
| Total volume | 30 μL |

Reaction condition: 20° C., 15 mins.

According to the instruction of the manufacturer, the reaction products were purified by using Ampure Beads (Beckman Coulter Genomics), and the purified products were dissolved in 17 μl deionized water. Agilent Bioanalyzer 2100 (Agilent Company) and Fluorescence quantitative PCR (QPCR) were used to detect the DNA concentration of the products, the results were as follow.

| | 2100 (nM) | qPCR (nM) |
| --- | --- | --- |
| HPV-1 Group | 20.4 | 24.2 |
| HPV-2 Group | 21.6 | 25.8 |

Example 5

Solexa Sequencing

The concentrations measured by Agilent Bioanalyzer 2100 were used as the standard, and the two products obtained in last step were mixed equimolarly (10 pmol DNA for each). According to the instruction of the manufacturer, Solexa sequencer (Illumina Genome Analyzer IIx sequencer) was used in sequencing under Solexa PE-75 program.

Example 6

Result Analysis

According to the sequence information of the characteristic sequences of the adapters and the index primers (index portion and primer portion) in the sequencing result, the sequencing results were corresponded to the samples one by one. Then, the sequencing result of each sample was aligned with HPV database by using alignment programs known in the art, such as BLAST and SOAP, thereby accomplishing HPV detection and accurately typing HPV.

The detection results obtained were completely identical to the known results (see Table 3), indicating that the method according to the present invention can be applied to accurately detect HPV in samples.

TABLE 3

Detection results of 190 samples.

| Sample No. | The known HC-II result (RLU/CO value) | HPV result of the present detection |
| --- | --- | --- |
| 1 | 14.2 | HPV56 |
| 2 | 0.31 | negative |
| 3 | 196.41 | HPV16 |
| 4 | 5.76 | HPV18 |
| 5 | 0.35 | negative |
| 6 | 99.86 | HPV18, HPV11, HPV16 |
| 7 | 128.86 | HPV39 |
| 8 | 35.12 | HPV18, HPV6 |
| 9 | 498.69 | HPV16, HPV56 |
| 10 | 603.57 | HPV18, HPV31, HPV39 |
| 11 | 0.27 | negative |
| 12 | 3420.57 | HPV18 |
| 13 | 0.38 | negative |
| 14 | 0.41 | negative |
| 15 | 455.06 | HPV16 |
| 16 | 8.93 | HPV18 |
| 17 | 0.6 | negative |
| 18 | 0.41 | negative |
| 19 | 0.29 | negative |
| 20 | 27.64 | HPV31 |
| 21 | 1985.41 | HPV56, HPV68 |
| 22 | 20.71 | HPV42 |
| 23 | 1795.83 | HPV11, HPV16, HPV52 |
| 24 | 9.55 | HPV43 |
| 25 | 237.62 | HPV39 |
| 26 | 1.5 | HPV6 |
| 27 | 1478.98 | HPV68, HPV16 |
| 28 | 115.31 | HPV44 |
| 29 | 419.31 | HPV16 |
| 30 | 1.81 | candHPV89 |
| 31 | 2013.61 | HPV52, HPV39 |
| 32 | 1379.09 | HPV54, HPV33 |
| 33 | 12.74 | HPV42 |
| 34 | 1695.31 | HPV16, candHPV89 |
| 35 | 1410.85 | HPV35 |
| 36 | 1149.25 | HPV18 |
| 37 | 0.24 | negative |
| 38 | 1.55 | HPV11 |
| 39 | 2.03 | HPV11, HPV6 |
| 40 | 8.45 | HPV42 |
| 41 | 0.2 | negative |
| 42 | 0.22 | negative |
| 43 | 0.53 | negative |
| 44 | 10.38 | HPV6 |
| 45 | 78.21 | HPV16 |
| 46 | 0.23 | negative |
| 47 | 45.42 | HPV16, HPV18 |
| 48 | 0.35 | negative |
| 49 | 148.66 | HPV18, candHPV89 |
| 50 | 60.27 | HPV56 |
| 51 | 0.28 | negative |
| 52 | 360.26 | HPV56, HPV68 |
| 53 | 50.31 | HPV18 |
| 54 | 0.18 | negative |
| 55 | 0.31 | negative |
| 56 | 196.41 | HPV16 |
| 57 | 5.76 | HPV51 |
| 58 | 0.23 | negative |
| 59 | 0.88 | negative |

TABLE 3-continued

Detection results of 190 samples.

| Sample No. | The known HC-II result (RLU/CO value) | HPV result of the present detection |
|---|---|---|
| 60 | 0.16 | negative |
| 61 | 870.63 | HPV52, HPV16 |
| 62 | 10.18 | HPV42 |
| 63 | 0.15 | negative |
| 64 | 1.36 | HPV11 |
| 65 | 68.2 | HPV59 |
| 66 | 0.68 | negative |
| 67 | 130.41 | HPV45 |
| 68 | 0.26 | negative |
| 69 | 5.25 | HPV6 |
| 70 | 0.46 | negative |
| 71 | 8.23 | HPV40 |
| 72 | 0.28 | negative |
| 73 | 100.16 | HPV43, HPV44 |
| 74 | 450.13 | HPV41 |
| 75 | 127.08 | HPV39, HPV6 |
| 76 | 602.79 | HPV45 |
| 77 | 276 | HPV16 |
| 78 | 243.6 | HPV6, HPV70, HPV39 |
| 79 | 229.44 | HPV35 |
| 80 | 1384.92 | HPV52, HPV56, HPV11 |
| 81 | 172.64 | HPV26, HPV42 |
| 82 | 855.24 | HPV35, HPV6 |
| 83 | 620.69 | HPV52 |
| 84 | 128.02 | HPV11 |
| 85 | 514.84 | HPV33 |
| 86 | 68.3 | HPV58 |
| 87 | 402.15 | HPV59, HPV16 |
| 88 | 51.72 | HPV33 |
| 89 | 1.78 | HPV6 |
| 90 | 56.7 | HPV11, HPV31 |
| 91 | 186.06 | HPV16 |
| 92 | 0.02 | negative |
| 93 | 386.06 | HPV18, HPV16 |
| 94 | 28.09 | HPV6, HPV44 |
| 95 | 186.06 | HPV68, |
| 96 | 0.28 | negative |
| 97 | 0.33 | negative |
| 98 | 181.29 | HPV35, HPV6 |
| 99 | 77.32 | HPV16 |
| 100 | 91.22 | HPV39 |
| 101 | 188.92 | HPV52 |
| 102 | 1352.83 | HPV35, HPV11, HPV39 |
| 103 | 1.39 | HPV43 |
| 104 | 119.5 | HPV45, HPV11 |
| 105 | 292.43 | HPV56, HPV31 |
| 106 | 2.91 | HPV68 |
| 107 | 193.13 | HPV45 |
| 108 | 2.62 | HPV6 |
| 109 | 94.12 | HPV16 |
| 110 | 792.72 | HPV18, HPV31 |
| 111 | 31.76 | HPV11 |
| 112 | 0.25 | negative |
| 113 | 0.23 | negative |
| 114 | 750.82 | HPV56, HPV16 |
| 115 | 0.4 | negative |
| 116 | 2.75 | HPV31 |
| 117 | 396.04 | HPV45 |
| 118 | 354.76 | HPV18, HPV16 |
| 119 | 6.26 | HPV11 |
| 120 | 1719.67 | HPV16, HPV45 |
| 121 | 76.92 | HPV51 |
| 122 | 1318.02 | HPV56, HPV16, HPV42 |
| 123 | 0.28 | negative |
| 124 | 0.33 | negative |
| 125 | 181.29 | HPV59 |
| 126 | 77.32 | HPV68 |
| 127 | 110.8 | HPV52 |
| 128 | 147.25 | HPV16 |
| 129 | 0.24 | HPV26 |
| 130 | 1.55 | HPV11, HPV53 |
| 131 | 2.03 | HPV6, HPV66 |
| 132 | 8.45 | HPV43 |
| 133 | 0.2 | negative |
| 134 | 0.24 | negative |
| 135 | 10.53 | HPV11 |
| 136 | 1410.85 | HPV16, HPV53, HPV70 |
| 137 | 1149.25 | HPV56, HPV81, HPV73 |
| 138 | 0.24 | negative |
| 139 | 413.9 | HPV45 |
| 140 | 17.05 | HPV11 |
| 141 | 23.6 | HPV52 |
| 142 | 3379.09 | HPV16, HPV35, HPV56 |
| 143 | 0.18 | negative |
| 144 | 1.46 | HPV18 |
| 145 | 1.25 | HPV11, HPV26 |
| 146 | 2.13 | HPV6, HPV81 |
| 147 | 872.52 | HPV16, HPV45, HPV52 |
| 148 | 1.5 | HPV18 |
| 149 | 4.33 | HPV16 |
| 150 | 0.82 | negative |
| 151 | 60.35 | HPV59 |
| 152 | 0.24 | negative |
| 153 | 0.23 | negative |
| 154 | 0.18 | negative |
| 155 | 1.46 | HPV51 |
| 156 | 11.25 | HPV16 |
| 157 | 2.13 | HPV11 |
| 158 | 0.13 | negative |
| 159 | 90.18 | HPV58 |
| 160 | 0.15 | negative |
| 161 | 602.79 | HPV68, HPV16 |
| 162 | 132.68 | HPV56, HPV11 |
| 163 | 127.08 | HPV39, HPV54 |
| 164 | 602.79 | HPV33 |
| 165 | 276 | HPV18 |
| 166 | 243.6 | HPV45 |
| 167 | 229.44 | HPV51 |
| 168 | 1384.92 | HPV16, HPV58, HPV72 |
| 169 | 172.64 | HPV58 |
| 170 | 855.24 | HPV16, candHPV89 |
| 171 | 126.47 | HPV51 |
| 172 | 86.62 | HPV44, HPV11 |
| 173 | 879.37 | HPV18, HPV58 |
| 174 | 119.39 | HPV56 |
| 175 | 0.61 | negative |
| 176 | 18.02 | HPV16 |
| 177 | 16.06 | HPV18 |
| 178 | 60.69 | HPV56, HPV11 |
| 179 | 2.45 | HPV11 |
| 180 | 94.93 | HPV39 |
| 181 | 1635.3 | HPV16, HPV35, HPV51 |
| 182 | 754.64 | HPV33, candHPV89 |
| 183 | 0.23 | HPV11 |
| 184 | 20.28 | HPV18 |
| 185 | 0.16 | negative |
| 186 | 0.13 | negative |
| 187 | 60.18 | HPV59 |
| 188 | 0.15 | negative |
| 189 | 1.36 | HPV43 |
| 190 | 0.28 | negative |

In addition, accurate typing of HPV in samples was also accomplished by the method according to the present invention. Table 4 provides the sequences and typing results of the samples corresponding to lane Nos. 1-14 as shown in FIG. 2.

TABLE 4

The sequences and typing results of the samples corresponding to lane Nos 1-14 as shown in FIG. 2.

| Lane No. | HPV type | Sequencing results | Parameter of alignment | | | SEQ ID NO: |
|---|---|---|---|---|---|---|
| | | | identity | score | e value | |
| 1 | HPV11 | GAAAAATAAACTGTAAATCATATTCCTCCACATGGCGCATGTATTCCTTATAATCTGAATTA | 96.77 | 107 | 6.00E-27 | 107 |
| 2 | HPV16 | TTTGTTACTGTGGTAGATACTACCCGCAGTACAAATATGTCATTATGTGCTGCCATATCTAC | 96.77 | 107 | 6.00E-27 | 108 |
| 3 | HPV18 | TTTGTTACTAAGGTAGATACCACTCGCAGTACCAATTTAACAATATGTGCTTCTACACAGTC | 96.77 | 107 | 6.00E-27 | 109 |
| 4 | HPV31 | GAAAAATAAACTGTAAATCATATTCCTCACCATGTCTTAAATACTCTTTAAAATTACTACTT | 95.16 | 99.6 | 2.00E-24 | 110 |
| 5 | HPV33 | GAAAAATAAACTGTAAATCATATTCCTCAACATGTCTTATATATTCTTTAAAATTTTCATTT | 96.77 | 107 | 6.00E-27 | 111 |
| 6 | HPV35 | GAAAAATAAACTGTAAATCATATTCTTCACCATGCCTTAAATATTCCTTATAATTGTCATTT | 98.39 | 115 | 3.00E-29 | 112 |
| 7 | HPV39 | TTTGTTACTGTGGTAGATACTACCCGTAGTACCAACTTTACATTATCTACCTCTATAGAGTC | 94.83 | 91.7 | 4.00E-22 | 113 |
| 8 | HPV43 | TTTGTTACTAAGGTAGATACCACTCGTAGTACAAACTTAACGTTATGTGCCTCTACTGACCC | 100 | 101 | 4.00E-25 | 114 |
| 9 | HPV45 | GAAAAATAAACTGTAAATCATATTCCTCCACATGTCTACTATAGTGCTTAAACTTAGTAGGA | 100 | 123 | 1.00E-31 | 115 |
| 10 | HPV51 | GAAATATAAATTGTAAATCAAATTCTTCCCCATGCCTAATATATTGCTTAAAGTTACTTGGA | 91.94 | 83.8 | 9.00E-20 | 116 |
| 11 | HPV52 | TTTGTTACTGTGGTGGATACTACTCGTAGCACTAACATGACTTTATGTGCTGAGGTTAAAAA | 98 | 91.7 | 4.00E-22 | 117 |
| 12 | HPV56 | TTTGTTACTGTTGTGGATACAACTAGAAGTACTAACATGACTATTAGTACTGCTACAGAACA | 95.16 | 99.6 | 2.00E-24 | 118 |
| 13 | HPV58 | GAAAAATAAACTGTAAATCATATTCCTCAACATGACGTACATATTCCTTAAAATTATCATTT | 96.77 | 107 | 6.00E-27 | 119 |
| 14 | HPV61 | TTTGTTACTGTGGTGGATACTACCCGCAGTACTAATTTAGCCATTTGCACTGCTACATCCCC | 94 | 75.8 | 2.00E-17 | 120 |

REFERENCES

The patents, publications and other materials, which are used to illustrate the present invention or provide further detailed contents about the practice of the present invention, are incorporated by reference herein, and are provided in the following list for the convenience.

[1]. Pectasides D, Kanposioras K, Papaxoinis G et al. Chemotherapy for recurrent cervical cancer. Cancer Treatment Reviews, 2008, 34(7): 603-613.
[2]. Brink, A. A., P. J. Snijders, and C. J. Meijer. HPV detection methods. Dis. Markers 2007, 23: 273-281.
[3]. IARC. Handbooks of cancer prevention. Cervix cancer screening [R]. Lyon: IARC Press, 2005.
[4]. Doorbar, J. Molecular biology of human papillomavirus infection and cervical cancer. Clin. Sci. 2006, 110: 525-541.
[5]. Cox T, Cuzick J. HPV DNA testing in cervical cancer screening: From evidence to policies. Gyneeol Oncol, 2006, 103: 8-11.
[6]. Kulmala S, syIjhen. Human papillomavirus testing with the hybrid capture assay and PCR as screening tools. Clin Microbiol, 2004, 42(6): 2470-2475.
[7]. Quail, M. et al., A large genome center's improvements to the Illumina sequencing system. Nat. Methods, 2008, 5, 1005-1010.
[8]. Brown, C. G. et al., Solexa/Illumina GAPipeline product and product documentation, Illumina Inc, 2006.
[9]. Lozano, R. Successfully integrating human papillomavirus testing into your practice. Arch. Pathol. Lab Med, 2003, 127: 991-994.

The invention claimed is:

1. A method for sequencing, detecting, or typing HPV in human samples, comprising the following steps:
   1) for each sample, amplifying DNA in the sample with one index primer group, wherein
      said index primer group comprises 11 index primers, the sequence of each of said index primers comprises an index sequence and a PCR primer sequence, and the index sequence is linked to 5' end of the PCR primer sequence, optionally via a linker sequence, wherein
      i) said index sequence is selected from the group consisting of SEQ ID NOS: 1-95, and each of said 11 index primers has the same index sequence, and
      ii) the PCR primer sequences of said 11 index primers consist of SEQ ID NOS: 96-106,
      wherein the index primer groups used in different samples are different, and different index primer groups employ different index sequences;
   2) mixing the amplification products obtained by conducting amplification with different index primer groups in step 1), so as to obtain one or more PCR product libraries;
   3) adding adapters to the one or more PCR product libraries obtained in step 2) by PCR-free methods, thereby constructing one or more sequencing libraries, wherein the adapters used in different sequencing libraries may be the same or different, and different adapters share the same sequencing sequence but have different characteristic sequences,
   4) optionally, mixing the sequencing libraries with different adapters obtained in step 3), so as to obtain one or more library mixtures;
   5) conducting sequencing of one or more sequencing libraries obtained in step 3) or one or more library mixtures obtained in step 4) by using a high throughput sequencing technology;
   6) correlating the sequencing results to the samples, according to the index primer sequences of the index primer group or according to the index primer sequences of the index primer group and the characteristic sequence of the adapter.

2. The method according to claim 1, wherein in step 3), the adapters are added to the amplification products in the PCR product libraries by using DNA ligase.

3. The method according to claim 1, wherein in step 5), the high throuhput sequencing technology is a paired-end sequencing technology.

4. The method according to claim 1, wherein in step 5), the high throughput sequencing technology is a sequencing by synthesis method.

5. The method according to claim 1, wherein said samples are exfoliative cells.

6. The method according to claim 1, wherein at least 50 index primer groups are used in step 1).

7. The method according to claim 1, wherein 95 index primer groups are used in step 1).

8. The method according to claim 1, wherein the index sequences used in step 1) comprise at least SEQ ID NOS: 1-10, or SEQ ID NOS: 11-20, or SEQ ID NOS: 21-30, or SEQ ID NOS: 31-40, or SEQ ID NOS: 41-50, or SEQ ID NOS: 51-60, or SEQ ID NOS: 61-70, or SEQ ID NOS: 71-80, or SEQ ID NOS: 81-90, or SEQ ID NOS: 91-95.

9. The method according to claim 1, wherein at least 50 adapters are used in step 3).

10. The method according to claim 1, wherein at least 200 adapters are used in step 3).

11. The method according to claim 1, wherein said adapters used in step 3) comprise a sequence selected from the group consisting of SEQ ID NOS: 121-132.

12. The method according to claim 1, further comprising aligning the sequencing results of said samples with sequence(s) in an HPV database to accurately type HPV in the samples.

* * * * *

SEQUENCE LISTING

<160> NUMBER OF SEQ ID NOS: 132

<210> SEQ ID NO 1
<211> LENGTH: 10

```
<212> TYPE: DNA
<213> ORGANISM: Artificial Sequence
<220> FEATURE:
<223> OTHER INFORMATION: Index sequence

<400> SEQUENCE: 1
gctgcgactc                                                            10

<210> SEQ ID NO 2
<211> LENGTH: 10
<212> TYPE: DNA
<213> ORGANISM: Artificial Sequence
<220> FEATURE:
<223> OTHER INFORMATION: Index sequence

<400> SEQUENCE: 2
gtgtagatac                                                            10

<210> SEQ ID NO 3
<211> LENGTH: 10
<212> TYPE: DNA
<213> ORGANISM: Artificial Sequence
<220> FEATURE:
<223> OTHER INFORMATION: Index sequence

<400> SEQUENCE: 3
ctgatatcta                                                            10

<210> SEQ ID NO 4
<211> LENGTH: 10
<212> TYPE: DNA
<213> ORGANISM: Artificial Sequence
<220> FEATURE:
<223> OTHER INFORMATION: Index sequence

<400> SEQUENCE: 4
acgatgctat                                                            10

<210> SEQ ID NO 5
<211> LENGTH: 10
<212> TYPE: DNA
<213> ORGANISM: Artificial Sequence
<220> FEATURE:
<223> OTHER INFORMATION: Index sequence

<400> SEQUENCE: 5
tagactagac                                                            10

<210> SEQ ID NO 6
<211> LENGTH: 10
<212> TYPE: DNA
<213> ORGANISM: Artificial Sequence
<220> FEATURE:
<223> OTHER INFORMATION: Index sequence

<400> SEQUENCE: 6
ctgtctgtgt                                                            10

<210> SEQ ID NO 7
<211> LENGTH: 10
<212> TYPE: DNA
<213> ORGANISM: Artificial Sequence
<220> FEATURE:
<223> OTHER INFORMATION: Index sequence

<400> SEQUENCE: 7
```
gcatactgac                                                          10

<210> SEQ ID NO 8
<211> LENGTH: 10
<212> TYPE: DNA
<213> ORGANISM: Artificial Sequence
<220> FEATURE:
<223> OTHER INFORMATION: Index sequence

<400> SEQUENCE: 8
ctgctcgcat                                                          10

<210> SEQ ID NO 9
<211> LENGTH: 10
<212> TYPE: DNA
<213> ORGANISM: Artificial Sequence
<220> FEATURE:
<223> OTHER INFORMATION: Index sequence

<400> SEQUENCE: 9
catgagtaga                                                          10

<210> SEQ ID NO 10
<211> LENGTH: 10
<212> TYPE: DNA
<213> ORGANISM: Artificial Sequence
<220> FEATURE:
<223> OTHER INFORMATION: Index sequence

<400> SEQUENCE: 10
tctcactatg                                                          10

<210> SEQ ID NO 11
<211> LENGTH: 10
<212> TYPE: DNA
<213> ORGANISM: Artificial Sequence
<220> FEATURE:
<223> OTHER INFORMATION: Index sequence

<400> SEQUENCE: 11
tgtactacta                                                          10

<210> SEQ ID NO 12
<211> LENGTH: 10
<212> TYPE: DNA
<213> ORGANISM: Artificial Sequence
<220> FEATURE:
<223> OTHER INFORMATION: Index sequence

<400> SEQUENCE: 12
gtagactagt                                                          10

<210> SEQ ID NO 13
<211> LENGTH: 10
<212> TYPE: DNA
<213> ORGANISM: Artificial Sequence
<220> FEATURE:
<223> OTHER INFORMATION: Index sequence

<400> SEQUENCE: 13
atatgctact                                                          10

<210> SEQ ID NO 14
<211> LENGTH: 10
<212> TYPE: DNA
<213> ORGANISM: Artificial Sequence

```
<220> FEATURE:
<223> OTHER INFORMATION: Index sequence

<400> SEQUENCE: 14
cactcgctgt                                                                10

<210> SEQ ID NO 15
<211> LENGTH: 10
<212> TYPE: DNA
<213> ORGANISM: Artificial Sequence
<220> FEATURE:
<223> OTHER INFORMATION: Index sequence

<400> SEQUENCE: 15
catcacgcac                                                                10

<210> SEQ ID NO 16
<211> LENGTH: 10
<212> TYPE: DNA
<213> ORGANISM: Artificial Sequence
<220> FEATURE:
<223> OTHER INFORMATION: Index sequence

<400> SEQUENCE: 16
agcatgtgat                                                                10

<210> SEQ ID NO 17
<211> LENGTH: 10
<212> TYPE: DNA
<213> ORGANISM: Artificial Sequence
<220> FEATURE:
<223> OTHER INFORMATION: Index sequence

<400> SEQUENCE: 17
agctagtaga                                                                10

<210> SEQ ID NO 18
<211> LENGTH: 10
<212> TYPE: DNA
<213> ORGANISM: Artificial Sequence
<220> FEATURE:
<223> OTHER INFORMATION: Index sequence

<400> SEQUENCE: 18
gctatgtagt                                                                10

<210> SEQ ID NO 19
<211> LENGTH: 10
<212> TYPE: DNA
<213> ORGANISM: Artificial Sequence
<220> FEATURE:
<223> OTHER INFORMATION: Index sequence

<400> SEQUENCE: 19
tacgatgatg                                                                10

<210> SEQ ID NO 20
<211> LENGTH: 10
<212> TYPE: DNA
<213> ORGANISM: Artificial Sequence
<220> FEATURE:
<223> OTHER INFORMATION: Index sequence

<400> SEQUENCE: 20
tacgctgtac                                                                10
```

```
<210> SEQ ID NO 21
<211> LENGTH: 10
<212> TYPE: DNA
<213> ORGANISM: Artificial Sequence
<220> FEATURE:
<223> OTHER INFORMATION: Index sequence

<400> SEQUENCE: 21
tatgtgtact                                                              10

<210> SEQ ID NO 22
<211> LENGTH: 10
<212> TYPE: DNA
<213> ORGANISM: Artificial Sequence
<220> FEATURE:
<223> OTHER INFORMATION: Index sequence

<400> SEQUENCE: 22
tgactcagac                                                              10

<210> SEQ ID NO 23
<211> LENGTH: 10
<212> TYPE: DNA
<213> ORGANISM: Artificial Sequence
<220> FEATURE:
<223> OTHER INFORMATION: Index sequence

<400> SEQUENCE: 23
tcgtagctca                                                              10

<210> SEQ ID NO 24
<211> LENGTH: 10
<212> TYPE: DNA
<213> ORGANISM: Artificial Sequence
<220> FEATURE:
<223> OTHER INFORMATION: Index sequence

<400> SEQUENCE: 24
gagactcgta                                                              10

<210> SEQ ID NO 25
<211> LENGTH: 10
<212> TYPE: DNA
<213> ORGANISM: Artificial Sequence
<220> FEATURE:
<223> OTHER INFORMATION: Index sequence

<400> SEQUENCE: 25
ctagatgtca                                                              10

<210> SEQ ID NO 26
<211> LENGTH: 10
<212> TYPE: DNA
<213> ORGANISM: Artificial Sequence
<220> FEATURE:
<223> OTHER INFORMATION: Index sequence

<400> SEQUENCE: 26
gatgactctc                                                              10

<210> SEQ ID NO 27
<211> LENGTH: 10
<212> TYPE: DNA
<213> ORGANISM: Artificial Sequence
<220> FEATURE:
<223> OTHER INFORMATION: Index sequence
```

<400> SEQUENCE: 27
tcagtcgcac                                                                 10

<210> SEQ ID NO 28
<211> LENGTH: 10
<212> TYPE: DNA
<213> ORGANISM: Artificial Sequence
<220> FEATURE:
<223> OTHER INFORMATION: Index sequence

<400> SEQUENCE: 28
tgtagtgagt                                                                 10

<210> SEQ ID NO 29
<211> LENGTH: 10
<212> TYPE: DNA
<213> ORGANISM: Artificial Sequence
<220> FEATURE:
<223> OTHER INFORMATION: Index sequence

<400> SEQUENCE: 29
tcatcgtaga                                                                 10

<210> SEQ ID NO 30
<211> LENGTH: 10
<212> TYPE: DNA
<213> ORGANISM: Artificial Sequence
<220> FEATURE:
<223> OTHER INFORMATION: Index sequence

<400> SEQUENCE: 30
tagcatctgt                                                                 10

<210> SEQ ID NO 31
<211> LENGTH: 10
<212> TYPE: DNA
<213> ORGANISM: Artificial Sequence
<220> FEATURE:
<223> OTHER INFORMATION: Index sequence

<400> SEQUENCE: 31
tagtagtcgt                                                                 10

<210> SEQ ID NO 32
<211> LENGTH: 10
<212> TYPE: DNA
<213> ORGANISM: Artificial Sequence
<220> FEATURE:
<223> OTHER INFORMATION: Index sequence

<400> SEQUENCE: 32
ctatacgtgc                                                                 10

<210> SEQ ID NO 33
<211> LENGTH: 10
<212> TYPE: DNA
<213> ORGANISM: Artificial Sequence
<220> FEATURE:
<223> OTHER INFORMATION: Index sequence

<400> SEQUENCE: 33
cgactgtaga                                                                 10

<210> SEQ ID NO 34

```
<211> LENGTH: 10
<212> TYPE: DNA
<213> ORGANISM: Artificial Sequence
<220> FEATURE:
<223> OTHER INFORMATION: Index sequence

<400> SEQUENCE: 34
gatgtcatgt                                                                10

<210> SEQ ID NO 35
<211> LENGTH: 10
<212> TYPE: DNA
<213> ORGANISM: Artificial Sequence
<220> FEATURE:
<223> OTHER INFORMATION: Index sequence

<400> SEQUENCE: 35
gtctcgactg                                                                10

<210> SEQ ID NO 36
<211> LENGTH: 10
<212> TYPE: DNA
<213> ORGANISM: Artificial Sequence
<220> FEATURE:
<223> OTHER INFORMATION: Index sequence

<400> SEQUENCE: 36
agctgacgat                                                                10

<210> SEQ ID NO 37
<211> LENGTH: 10
<212> TYPE: DNA
<213> ORGANISM: Artificial Sequence
<220> FEATURE:
<223> OTHER INFORMATION: Index sequence

<400> SEQUENCE: 37
atgatatagt                                                                10

<210> SEQ ID NO 38
<211> LENGTH: 10
<212> TYPE: DNA
<213> ORGANISM: Artificial Sequence
<220> FEATURE:
<223> OTHER INFORMATION: Index sequence

<400> SEQUENCE: 38
atgtgctcta                                                                10

<210> SEQ ID NO 39
<211> LENGTH: 10
<212> TYPE: DNA
<213> ORGANISM: Artificial Sequence
<220> FEATURE:
<223> OTHER INFORMATION: Index sequence

<400> SEQUENCE: 39
ctcactcgat                                                                10

<210> SEQ ID NO 40
<211> LENGTH: 10
<212> TYPE: DNA
<213> ORGANISM: Artificial Sequence
<220> FEATURE:
<223> OTHER INFORMATION: Index sequence

<400> SEQUENCE: 40
```

```
gctgcgactc                                                            10

<210> SEQ ID NO 41
<211> LENGTH: 10
<212> TYPE: DNA
<213> ORGANISM: Artificial Sequence
<220> FEATURE:
<223> OTHER INFORMATION: Index sequence

<400> SEQUENCE: 41
gagtcatgtc                                                            10

<210> SEQ ID NO 42
<211> LENGTH: 10
<212> TYPE: DNA
<213> ORGANISM: Artificial Sequence
<220> FEATURE:
<223> OTHER INFORMATION: Index sequence

<400> SEQUENCE: 42
catacgctca                                                            10

<210> SEQ ID NO 43
<211> LENGTH: 10
<212> TYPE: DNA
<213> ORGANISM: Artificial Sequence
<220> FEATURE:
<223> OTHER INFORMATION: Index sequence

<400> SEQUENCE: 43
cactctcgtc                                                            10

<210> SEQ ID NO 44
<211> LENGTH: 10
<212> TYPE: DNA
<213> ORGANISM: Artificial Sequence
<220> FEATURE:
<223> OTHER INFORMATION: Index sequence

<400> SEQUENCE: 44
gcactagatg                                                            10

<210> SEQ ID NO 45
<211> LENGTH: 10
<212> TYPE: DNA
<213> ORGANISM: Artificial Sequence
<220> FEATURE:
<223> OTHER INFORMATION: Index sequence

<400> SEQUENCE: 45
agtacgcatg                                                            10

<210> SEQ ID NO 46
<211> LENGTH: 10
<212> TYPE: DNA
<213> ORGANISM: Artificial Sequence
<220> FEATURE:
<223> OTHER INFORMATION: Index sequence

<400> SEQUENCE: 46
tctgtgacgt                                                            10

<210> SEQ ID NO 47
<211> LENGTH: 10
<212> TYPE: DNA
```

```
<213> ORGANISM: Artificial Sequence
<220> FEATURE:
<223> OTHER INFORMATION: Index sequence

<400> SEQUENCE: 47
tagctcatct                                                          10

<210> SEQ ID NO 48
<211> LENGTH: 10
<212> TYPE: DNA
<213> ORGANISM: Artificial Sequence
<220> FEATURE:
<223> OTHER INFORMATION: Index sequence

<400> SEQUENCE: 48
agcatacact                                                          10

<210> SEQ ID NO 49
<211> LENGTH: 10
<212> TYPE: DNA
<213> ORGANISM: Artificial Sequence
<220> FEATURE:
<223> OTHER INFORMATION: Index sequence

<400> SEQUENCE: 49
gctatagtca                                                          10

<210> SEQ ID NO 50
<211> LENGTH: 10
<212> TYPE: DNA
<213> ORGANISM: Artificial Sequence
<220> FEATURE:
<223> OTHER INFORMATION: Index sequence

<400> SEQUENCE: 50
cgtctcatgc                                                          10

<210> SEQ ID NO 51
<211> LENGTH: 10
<212> TYPE: DNA
<213> ORGANISM: Artificial Sequence
<220> FEATURE:
<223> OTHER INFORMATION: Index sequence

<400> SEQUENCE: 51
gctactacgt                                                          10

<210> SEQ ID NO 52
<211> LENGTH: 10
<212> TYPE: DNA
<213> ORGANISM: Artificial Sequence
<220> FEATURE:
<223> OTHER INFORMATION: Index sequence

<400> SEQUENCE: 52
gagtgtacta                                                          10

<210> SEQ ID NO 53
<211> LENGTH: 10
<212> TYPE: DNA
<213> ORGANISM: Artificial Sequence
<220> FEATURE:
<223> OTHER INFORMATION: Index sequence

<400> SEQUENCE: 53
gtcatacgtg                                                          10
```

```
<210> SEQ ID NO 54
<211> LENGTH: 10
<212> TYPE: DNA
<213> ORGANISM: Artificial Sequence
<220> FEATURE:
<223> OTHER INFORMATION: Index sequence

<400> SEQUENCE: 54
tatgagagat                                                                10

<210> SEQ ID NO 55
<211> LENGTH: 10
<212> TYPE: DNA
<213> ORGANISM: Artificial Sequence
<220> FEATURE:
<223> OTHER INFORMATION: Index sequence

<400> SEQUENCE: 55
atctgagtac                                                                10

<210> SEQ ID NO 56
<211> LENGTH: 10
<212> TYPE: DNA
<213> ORGANISM: Artificial Sequence
<220> FEATURE:
<223> OTHER INFORMATION: Index sequence

<400> SEQUENCE: 56
cgatagcatc                                                                10

<210> SEQ ID NO 57
<211> LENGTH: 10
<212> TYPE: DNA
<213> ORGANISM: Artificial Sequence
<220> FEATURE:
<223> OTHER INFORMATION: Index sequence

<400> SEQUENCE: 57
actgatctca                                                                10

<210> SEQ ID NO 58
<211> LENGTH: 10
<212> TYPE: DNA
<213> ORGANISM: Artificial Sequence
<220> FEATURE:
<223> OTHER INFORMATION: Index sequence

<400> SEQUENCE: 58
ctcgatacta                                                                10

<210> SEQ ID NO 59
<211> LENGTH: 10
<212> TYPE: DNA
<213> ORGANISM: Artificial Sequence
<220> FEATURE:
<223> OTHER INFORMATION: Index sequence

<400> SEQUENCE: 59
catgtgactg                                                                10

<210> SEQ ID NO 60
<211> LENGTH: 10
<212> TYPE: DNA
<213> ORGANISM: Artificial Sequence
<220> FEATURE:
```

<223> OTHER INFORMATION: Index sequence

<400> SEQUENCE: 60
cgcatcacta                                                          10

<210> SEQ ID NO 61
<211> LENGTH: 10
<212> TYPE: DNA
<213> ORGANISM: Artificial Sequence
<220> FEATURE:
<223> OTHER INFORMATION: Index sequence

<400> SEQUENCE: 61
gcatatatct                                                          10

<210> SEQ ID NO 62
<211> LENGTH: 10
<212> TYPE: DNA
<213> ORGANISM: Artificial Sequence
<220> FEATURE:
<223> OTHER INFORMATION: Index sequence

<400> SEQUENCE: 62
ctgatgcgac                                                          10

<210> SEQ ID NO 63
<211> LENGTH: 10
<212> TYPE: DNA
<213> ORGANISM: Artificial Sequence
<220> FEATURE:
<223> OTHER INFORMATION: Index sequence

<400> SEQUENCE: 63
tctcagagtc                                                          10

<210> SEQ ID NO 64
<211> LENGTH: 10
<212> TYPE: DNA
<213> ORGANISM: Artificial Sequence
<220> FEATURE:
<223> OTHER INFORMATION: Index sequence

<400> SEQUENCE: 64
cagtgcgagt                                                          10

<210> SEQ ID NO 65
<211> LENGTH: 10
<212> TYPE: DNA
<213> ORGANISM: Artificial Sequence
<220> FEATURE:
<223> OTHER INFORMATION: Index sequence

<400> SEQUENCE: 65
atctctgatg                                                          10

<210> SEQ ID NO 66
<211> LENGTH: 10
<212> TYPE: DNA
<213> ORGANISM: Artificial Sequence
<220> FEATURE:
<223> OTHER INFORMATION: Index sequence

<400> SEQUENCE: 66
gctagtagtc                                                          10

```
<210> SEQ ID NO 67
<211> LENGTH: 10
<212> TYPE: DNA
<213> ORGANISM: Artificial Sequence
<220> FEATURE:
<223> OTHER INFORMATION: Index sequence

<400> SEQUENCE: 67
atgagtcgtc                                                          10

<210> SEQ ID NO 68
<211> LENGTH: 10
<212> TYPE: DNA
<213> ORGANISM: Artificial Sequence
<220> FEATURE:
<223> OTHER INFORMATION: Index sequence

<400> SEQUENCE: 68
atcactcaga                                                          10

<210> SEQ ID NO 69
<211> LENGTH: 10
<212> TYPE: DNA
<213> ORGANISM: Artificial Sequence
<220> FEATURE:
<223> OTHER INFORMATION: Index sequence

<400> SEQUENCE: 69
tctctctgat                                                          10

<210> SEQ ID NO 70
<211> LENGTH: 10
<212> TYPE: DNA
<213> ORGANISM: Artificial Sequence
<220> FEATURE:
<223> OTHER INFORMATION: Index sequence

<400> SEQUENCE: 70
ctctagtgct                                                          10

<210> SEQ ID NO 71
<211> LENGTH: 10
<212> TYPE: DNA
<213> ORGANISM: Artificial Sequence
<220> FEATURE:
<223> OTHER INFORMATION: Index sequence

<400> SEQUENCE: 71
cgtcgtgcta                                                          10

<210> SEQ ID NO 72
<211> LENGTH: 10
<212> TYPE: DNA
<213> ORGANISM: Artificial Sequence
<220> FEATURE:
<223> OTHER INFORMATION: Index sequence

<400> SEQUENCE: 72
cgactactat                                                          10

<210> SEQ ID NO 73
<211> LENGTH: 10
<212> TYPE: DNA
<213> ORGANISM: Artificial Sequence
<220> FEATURE:
<223> OTHER INFORMATION: Index sequence
```

```
<400> SEQUENCE: 73
gcacgtcgat                                                              10

<210> SEQ ID NO 74
<211> LENGTH: 10
<212> TYPE: DNA
<213> ORGANISM: Artificial Sequence
<220> FEATURE:
<223> OTHER INFORMATION: Index sequence

<400> SEQUENCE: 74
gtagtgctct                                                              10

<210> SEQ ID NO 75
<211> LENGTH: 10
<212> TYPE: DNA
<213> ORGANISM: Artificial Sequence
<220> FEATURE:
<223> OTHER INFORMATION: Index sequence

<400> SEQUENCE: 75
ctgacgagct                                                              10

<210> SEQ ID NO 76
<211> LENGTH: 10
<212> TYPE: DNA
<213> ORGANISM: Artificial Sequence
<220> FEATURE:
<223> OTHER INFORMATION: Index sequence

<400> SEQUENCE: 76
ctatagtcta                                                              10

<210> SEQ ID NO 77
<211> LENGTH: 10
<212> TYPE: DNA
<213> ORGANISM: Artificial Sequence
<220> FEATURE:
<223> OTHER INFORMATION: Index sequence

<400> SEQUENCE: 77
acacgcacta                                                              10

<210> SEQ ID NO 78
<211> LENGTH: 10
<212> TYPE: DNA
<213> ORGANISM: Artificial Sequence
<220> FEATURE:
<223> OTHER INFORMATION: Index sequence

<400> SEQUENCE: 78
ctcgcactac                                                              10

<210> SEQ ID NO 79
<211> LENGTH: 10
<212> TYPE: DNA
<213> ORGANISM: Artificial Sequence
<220> FEATURE:
<223> OTHER INFORMATION: Index sequence

<400> SEQUENCE: 79
agatctcact                                                              10

<210> SEQ ID NO 80
<211> LENGTH: 10
```

```
<212> TYPE: DNA
<213> ORGANISM: Artificial Sequence
<220> FEATURE:
<223> OTHER INFORMATION: Index sequence

<400> SEQUENCE: 80
atactagtgt                                                          10

<210> SEQ ID NO 81
<211> LENGTH: 10
<212> TYPE: DNA
<213> ORGANISM: Artificial Sequence
<220> FEATURE:
<223> OTHER INFORMATION: Index sequence

<400> SEQUENCE: 81
atatctcgta                                                          10

<210> SEQ ID NO 82
<211> LENGTH: 10
<212> TYPE: DNA
<213> ORGANISM: Artificial Sequence
<220> FEATURE:
<223> OTHER INFORMATION: Index sequence

<400> SEQUENCE: 82
tgactgcgta                                                          10

<210> SEQ ID NO 83
<211> LENGTH: 10
<212> TYPE: DNA
<213> ORGANISM: Artificial Sequence
<220> FEATURE:
<223> OTHER INFORMATION: Index sequence

<400> SEQUENCE: 83
tgtagacgta                                                          10

<210> SEQ ID NO 84
<211> LENGTH: 10
<212> TYPE: DNA
<213> ORGANISM: Artificial Sequence
<220> FEATURE:
<223> OTHER INFORMATION: Index sequence

<400> SEQUENCE: 84
agagactatg                                                          10

<210> SEQ ID NO 85
<211> LENGTH: 10
<212> TYPE: DNA
<213> ORGANISM: Artificial Sequence
<220> FEATURE:
<223> OTHER INFORMATION: Index sequence

<400> SEQUENCE: 85
gtcgagtcac                                                          10

<210> SEQ ID NO 86
<211> LENGTH: 10
<212> TYPE: DNA
<213> ORGANISM: Artificial Sequence
<220> FEATURE:
<223> OTHER INFORMATION: Index sequence

<400> SEQUENCE: 86
```

-continued tgacagctac                                                    10

<210> SEQ ID NO 87
<211> LENGTH: 10
<212> TYPE: DNA
<213> ORGANISM: Artificial Sequence
<220> FEATURE:
<223> OTHER INFORMATION: Index sequence

<400> SEQUENCE: 87
cgctagacat                                                    10

<210> SEQ ID NO 88
<211> LENGTH: 10
<212> TYPE: DNA
<213> ORGANISM: Artificial Sequence
<220> FEATURE:
<223> OTHER INFORMATION: Index sequence

<400> SEQUENCE: 88
cgtagatatg                                                    10

<210> SEQ ID NO 89
<211> LENGTH: 10
<212> TYPE: DNA
<213> ORGANISM: Artificial Sequence
<220> FEATURE:
<223> OTHER INFORMATION: Index sequence

<400> SEQUENCE: 89
tgagtctgct                                                    10

<210> SEQ ID NO 90
<211> LENGTH: 10
<212> TYPE: DNA
<213> ORGANISM: Artificial Sequence
<220> FEATURE:
<223> OTHER INFORMATION: Index sequence

<400> SEQUENCE: 90
tagtcgtatg                                                    10

<210> SEQ ID NO 91
<211> LENGTH: 10
<212> TYPE: DNA
<213> ORGANISM: Artificial Sequence
<220> FEATURE:
<223> OTHER INFORMATION: Index sequence

<400> SEQUENCE: 91
catacacgac                                                    10

<210> SEQ ID NO 92
<211> LENGTH: 10
<212> TYPE: DNA
<213> ORGANISM: Artificial Sequence
<220> FEATURE:
<223> OTHER INFORMATION: Index sequence

<400> SEQUENCE: 92
cgctcagaga                                                    10

<210> SEQ ID NO 93
<211> LENGTH: 10
<212> TYPE: DNA
<213> ORGANISM: Artificial Sequence
<220> FEATURE:
<223> OTHER INFORMATION: Index sequence

<400> SEQUENCE: 93 gtgagtctca					10

<210> SEQ ID NO 94
<211> LENGTH: 10
<212> TYPE: DNA
<213> ORGANISM: Artificial Sequence
<220> FEATURE:
<223> OTHER INFORMATION: Index sequence

<400> SEQUENCE: 94 gacagatgat					10

<210> SEQ ID NO 95
<211> LENGTH: 10
<212> TYPE: DNA
<213> ORGANISM: Artificial Sequence
<220> FEATURE:
<223> OTHER INFORMATION: Index sequence

<400> SEQUENCE: 95 gctgtgcgac					10

<210> SEQ ID NO 96
<211> LENGTH: 23
<212> TYPE: DNA
<213> ORGANISM: Artificial Sequence
<220> FEATURE:
<223> OTHER INFORMATION: PCR primer

<400> SEQUENCE: 96
tttgttactg tggtagatac tac					23

<210> SEQ ID NO 97
<211> LENGTH: 23
<212> TYPE: DNA
<213> ORGANISM: Artificial Sequence
<220> FEATURE:
<223> OTHER INFORMATION: PCR primer

<400> SEQUENCE: 97
tttgttactg tggtggatac tac					23

<210> SEQ ID NO 98
<211> LENGTH: 23
<212> TYPE: DNA
<213> ORGANISM: Artificial Sequence
<220> FEATURE:
<223> OTHER INFORMATION: PCR primer

<400> SEQUENCE: 98
tttgttaccg ttgttgatac tac					23

<210> SEQ ID NO 99
<211> LENGTH: 25
<212> TYPE: DNA
<213> ORGANISM: Artificial Sequence
<220> FEATURE:
<223> OTHER INFORMATION: PCR primer

<400> SEQUENCE: 99
tttgttacta aggtagatac cactc					25

<210> SEQ ID NO 100
<211> LENGTH: 23
<212> TYPE: DNA
<213> ORGANISM: Artificial Sequence
<220> FEATURE:
<223> OTHER INFORMATION: PCR primer

<400> SEQUENCE: 100
tttgttactg ttgtggatac aac                                              23

<210> SEQ ID NO 101
<211> LENGTH: 25
<212> TYPE: DNA
<213> ORGANISM: Artificial Sequence
<220> FEATURE:
<223> OTHER INFORMATION: PCR primer

<400> SEQUENCE: 101
tttgttacta tggtagatac cacac                                            25

<210> SEQ ID NO 102
<211> LENGTH: 27
<212> TYPE: DNA
<213> ORGANISM: Artificial Sequence
<220> FEATURE:
<223> OTHER INFORMATION: PCR primer

<400> SEQUENCE: 102
gaaaaataaa ctgtaaatca tattcct                                          27

<210> SEQ ID NO 103
<211> LENGTH: 25
<212> TYPE: DNA
<213> ORGANISM: Artificial Sequence
<220> FEATURE:
<223> OTHER INFORMATION: PCR primer

<400> SEQUENCE: 103
gaaaaataaa ttgtaaatca tactc                                            25

<210> SEQ ID NO 104
<211> LENGTH: 25
<212> TYPE: DNA
<213> ORGANISM: Artificial Sequence
<220> FEATURE:
<223> OTHER INFORMATION: PCR primer

<400> SEQUENCE: 104
gaaatataaa ttgtaaatca aattc                                            25

<210> SEQ ID NO 105
<211> LENGTH: 25
<212> TYPE: DNA
<213> ORGANISM: Artificial Sequence
<220> FEATURE:
<223> OTHER INFORMATION: PCR primer

<400> SEQUENCE: 105
gaaaaataaa ctgtaaatca tattc                                            25

<210> SEQ ID NO 106
<211> LENGTH: 25
<212> TYPE: DNA
<213> ORGANISM: Artificial Sequence
<220> FEATURE:
<223> OTHER INFORMATION: PCR primer

```
<400> SEQUENCE: 106
gaaaaataaa ctgcaaatca tattc                                    25

<210> SEQ ID NO 107
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 107
gaaaaataaa ctgtaaatca tattcctcca catggcgcat gtattcctta taatctgaat   60
ta                                                             62

<210> SEQ ID NO 108
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 108
tttgttactg tggtagatac tacccgcagt acaaatatgt cattatgtgc tgccatatct   60
ac                                                             62

<210> SEQ ID NO 109
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 109
tttgttacta aggtagatac cactcgcagt accaatttaa caatatgtgc ttctacacag   60
tc                                                             62

<210> SEQ ID NO 110
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 110
gaaaaataaa ctgtaaatca tattcctcac catgtcttaa atactcttta aaattactac   60
tt                                                             62

<210> SEQ ID NO 111
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 111
gaaaaataaa ctgtaaatca tattcctcaa catgtcttat atattcttta aaattttcat   60
tt                                                             62

<210> SEQ ID NO 112
<211> LENGTH: 62
<212> TYPE: DNA
```

<213> ORGANISM: Artificial Sequence
<220> FEATURE:
<223> OTHER INFORMATION: HPV DNA sequence

<400> SEQUENCE: 112

```
gaaaaataaa ctgtaaatca tattcttcac catgccttaa atattcctta taattgtcat    60
tt                                                                    62
```

<210> SEQ ID NO 113
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 113

```
tttgttactg tggtagatac tacccgtagt accaacttta cattatctac ctctatagag    60
tc                                                                    62
```

<210> SEQ ID NO 114
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 114

```
tttgttacta aggtagatac cactcgtagt acaaacttaa cgttatgtgc ctctactgac    60
cc                                                                    62
```

<210> SEQ ID NO 115
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 115

```
gaaaaataaa ctgtaaatca tattcctcca catgtctact atagtgctta aacttagtag    60
ga                                                                    62
```

<210> SEQ ID NO 116
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 116

```
gaaatataaa ttgtaaatca aattcttccc catgcctaat atattgctta aagttacttg    60
ga                                                                    62
```

<210> SEQ ID NO 117
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 117

```
tttgttactg tggtggatac tactcgtagc actaacatga ctttatgtgc tgaggttaaa    60
aa                                                                    62
```

<210> SEQ ID NO 118
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 118
tttgttactg ttgtggatac aactagaagt actaacatga ctattagtac tgctacagaa    60
ca    62

<210> SEQ ID NO 119
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 119
gaaaaataaa ctgtaaatca tattcctcaa catgacgtac atattcctta aaattatcat    60
tt    62

<210> SEQ ID NO 120
<211> LENGTH: 62
<212> TYPE: DNA
<213> ORGANISM: Artificial Sequence
<220> FEATURE:
<223> OTHER INFORMATION: HPV DNA sequence

<400> SEQUENCE: 120
tttgttactg tggtggatac tacccgcagt actaatttag ccatttgcac tgctacatcc    60
cc    62

<210> SEQ ID NO 121
<211> LENGTH: 63
<212> TYPE: DNA
<213> ORGANISM: Artificial Sequence
<220> FEATURE:
<223> OTHER INFORMATION: adapter sequence

<400> SEQUENCE: 121
gatcggaaga gcacacgtct gaactccagt cacatcacga tctcgtatgc cgtcttctgc    60
ttg    63

<210> SEQ ID NO 122
<211> LENGTH: 63
<212> TYPE: DNA
<213> ORGANISM: Artificial Sequence
<220> FEATURE:
<223> OTHER INFORMATION: adapter sequence

<400> SEQUENCE: 122
gatcggaaga gcacacgtct gaactccagt caccgatgta tctcgtatgc cgtcttctgc    60
ttg    63

<210> SEQ ID NO 123
<211> LENGTH: 63
<212> TYPE: DNA
<213> ORGANISM: Artificial Sequence
<220> FEATURE:
<223> OTHER INFORMATION: adapter sequence

```
<400> SEQUENCE: 123
gatcggaaga gcacacgtct gaactccagt cacttaggca tctcgtatgc cgtcttctgc    60
ttg                                                                 63

<210> SEQ ID NO 124
<211> LENGTH: 63
<212> TYPE: DNA
<213> ORGANISM: Artificial Sequence
<220> FEATURE:
<223> OTHER INFORMATION: adapter sequence

<400> SEQUENCE: 124
gatcggaaga gcacacgtct gaactccagt cactgaccaa tctcgtatgc cgtcttctgc    60
ttg                                                                 63

<210> SEQ ID NO 125
<211> LENGTH: 63
<212> TYPE: DNA
<213> ORGANISM: Artificial Sequence
<220> FEATURE:
<223> OTHER INFORMATION: adapter sequence

<400> SEQUENCE: 125
gatcggaaga gcacacgtct gaactccagt cacacagtga tctcgtatgc cgtcttctgc    60
ttg                                                                 63

<210> SEQ ID NO 126
<211> LENGTH: 63
<212> TYPE: DNA
<213> ORGANISM: Artificial Sequence
<220> FEATURE:
<223> OTHER INFORMATION: adapter sequence

<400> SEQUENCE: 126
gatcggaaga gcacacgtct gaactccagt cacgccaata tctcgtatgc cgtcttctgc    60
ttg                                                                 63

<210> SEQ ID NO 127
<211> LENGTH: 63
<212> TYPE: DNA
<213> ORGANISM: Artificial Sequence
<220> FEATURE:
<223> OTHER INFORMATION: adapter sequence

<400> SEQUENCE: 127
gatcggaaga gcacacgtct gaactccagt caccagatca tctcgtatgc cgtcttctgc    60
ttg                                                                 63

<210> SEQ ID NO 128
<211> LENGTH: 63
<212> TYPE: DNA
<213> ORGANISM: Artificial Sequence
<220> FEATURE:
<223> OTHER INFORMATION: adapter sequence

<400> SEQUENCE: 128
gatcggaaga gcacacgtct gaactccagt cacacttgaa tctcgtatgc cgtcttctgc    60
ttg                                                                 63

<210> SEQ ID NO 129
<211> LENGTH: 63
```

```
<212> TYPE: DNA
<213> ORGANISM: Artificial Sequence
<220> FEATURE:
<223> OTHER INFORMATION: adapter sequence

<400> SEQUENCE: 129
gatcggaaga gcacacgtct gaactccagt cacgatcaga tctcgtatgc cgtcttctgc    60
ttg                                                                 63

<210> SEQ ID NO 130
<211> LENGTH: 63
<212> TYPE: DNA
<213> ORGANISM: Artificial Sequence
<220> FEATURE:
<223> OTHER INFORMATION: adapter sequence

<400> SEQUENCE: 130
gatcggaaga gcacacgtct gaactccagt cactagctta tctcgtatgc cgtcttctgc    60
ttg                                                                 63

<210> SEQ ID NO 131
<211> LENGTH: 63
<212> TYPE: DNA
<213> ORGANISM: Artificial Sequence
<220> FEATURE:
<223> OTHER INFORMATION: adapter sequence

<400> SEQUENCE: 131
gatcggaaga gcacacgtct gaactccagt cacggctaca tctcgtatgc cgtcttctgc    60
ttg                                                                 63

<210> SEQ ID NO 132
<211> LENGTH: 63
<212> TYPE: DNA
<213> ORGANISM: Artificial Sequence
<220> FEATURE:
<223> OTHER INFORMATION: adapter sequence

<400> SEQUENCE: 132
gatcggaaga gcacacgtct gaactccagt caccttgtaa tctcgtatgc cgtcttctgc    60
ttg                                                                 63
```